United States Patent
Collins et al.

(10) Patent No.: US 6,352,994 B2
(45) Date of Patent: Mar. 5, 2002

(54) SUBSTITUTED 1H-PYRIDINYL-2-ONES AS GABA$_A$ ALPHA 2/3 LIGANDS

(75) Inventors: Ian James Collins, Ware; Stephen Robert Fletcher, Hatfield Heath; Timothy Harrison, Great Dunmow; Paul David Leeson, Congerstone; Christopher Richard Moyes, Sawbridgeworth; Alan John Nadin, Cambridge; Michael Rowley, Chelmsford; Timothy Jason Sparey, Sawbridgeworth; Martin Richard Teall, Bishops Stortford, all of (GB)

(73) Assignee: Merck Sharp & Dohme Limited, Hoddesdon (GB)

( * ) Notice: Subject to any disclaimer, the term of this patent is extended or adjusted under 35 U.S.C. 154(b) by 0 days.

(21) Appl. No.: 09/754,092

(22) Filed: Jan. 4, 2001

Related U.S. Application Data

(62) Division of application No. 09/423,178, filed as application No. PCT/GB98/01593 on Jun. 1, 1998, now Pat. No. 6,200,982.

(51) Int. Cl.$^7$ .................. A61K 31/435; A61K 31/505; A61K 31/40; C07D 239/01; C07D 213/00
(52) U.S. Cl. .................. 514/277; 514/183; 514/256; 514/408; 546/1; 546/24
(58) Field of Search ................. 514/277, 256, 514/408, 183; 544/242; 546/1, 24

(56) References Cited

PUBLICATIONS

Froelind B. Et al. J. Med. Chem. 38/17, 3287–96 Nov. 1995.*

Im, H. K., et al., Molecular Pharm., vol. 44, No. 2, pp. 468–472 (1993).

Froelund, B., et al., J. Medicinal Chem., vol. 38, No. 17, pp. 3287–3296 (1995).

Matsuyama, K, et al., Adv. Behav. Biol., vol. 36, pp. 185–196 (1989).

Nishio, T., et al., Tetrahedron Letters, vol. 27, No. 46, pp. 5637–5640 (1986).

Cheeseman, G. W. H., J. Chemical Society, vol. 18, pp. 2977–2979 (1971).

* cited by examiner

*Primary Examiner*—Mukund J. Shah
*Assistant Examiner*—Sudhaker Patel
(74) *Attorney, Agent, or Firm*—Shu Muk Lee; David L. Rose

(57) ABSTRACT

Compounds according to Formula (I) or a salt thereof are selective ligands for GABA$_A$ receptors useful for treatment of disorders of the central nervous system:

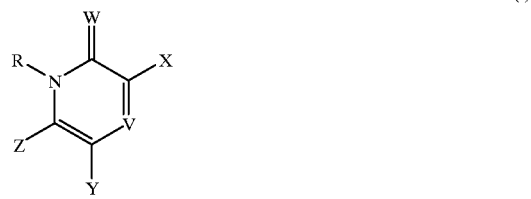

8 Claims, No Drawings

SUBSTITUTED 1H-PYRIDINYL-2-ONES AS GABA$_A$ ALPHA 2/3 LIGANDS

This is a divisional of U.S. patent application Ser. No. 09/423,178, filed Feb. 11, 2000 now 6,200,982 which is an Application under 35 USC 371 of PCT/GB98/01593, filed Jun. 1, 1998, which claims the benefit of GB 9711753.5 filed Jun. 6, 1997.

BACKGROUND OF THE INVENTION

The present invention relates to a class of substituted 1H-pyridinyl-2-one derivatives and to their use in therapy. More particularly, this invention is concerned with substituted 1H-pyridinyl-2-one derivatives which are ligands for GABA$_A$ receptors and are therefore useful in the therapy of deleterious mental states.

Receptors for the major inhibitory neurotransmitter, gamma-aminobutyric acid (GABA), are divided into two main classes: (1) GABA$_A$ receptors, which are members of the ligand-gated ion channel superfamily; and (2) GABA$_B$ receptors, which may be members of the G-protein linked receptor superfamily. Since the first cDNAs encoding individual GABA$_A$ receptor subunits were cloned the number of known members of the mammalian family has grown to thirteen (six α subunits, three β subunits, three γ subunits and one δ subunit). It may be that further subunits remain to be discovered; however, none has been reported since 1993.

Although knowledge of the diversity of the GABA$_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional GABA$_A$ receptor expressed by transiently transfecting cDNAs into cells. As indicated above, a δ subunit also exists, but is present only to a minor extent in GABA$_A$ receptor populations.

Studies of receptor size and visualisation by electron microscopy conclude that, like other members of the ligand-gated ion channel family, the native GABA$_A$ receptor-exists in pentameric form. The selection of at least one α, one β and one γ subunit from a repertoire of thirteen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, α1β2γ2, α2β2/3γ2, α3βγ2/3, α2βγ1, α5β3γ2/3, α6βγ2, α6βδ and α4βδ. Subtype assemblies containing an α1 subunit are present in most areas of the brain and are thought to account for over 40% of GABA$_A$ receptors in the rat. Subtype assemblies containing α2 and α3 subunits respectively are thought to account for about 25% and 17% of GABA$_A$ receptors in the rat. Subtype assemblies containing an α5 subunit are expressed predominantly in the hippocampus and cortex and are thought to represent about 4% of GABA$_A$ receptors in the rat.

A characteristic property of all known GABA$_A$ receptors is the presence of a number of modulatory sites, one of which is the benzodiazepine (BZ) binding site. The BZ binding site is the most explored of the GABA$_A$ receptor modulatory sites, and is the site through which anxiolytic drugs such as diazepam and temazepam exert their effect. Before the cloning of the GABA$_A$ receptor gene family, the benzodiazepine binding site was historically subdivided into two subtypes, BZ1 and BZ2, on the basis of radioligand binding studies. The BZ1 subtype has been shown to be pharmacologically equivalent to a GABA$_A$ receptor comprising the α1 subunit in combination with a β subunit and γ2. This is the most abundant GABA$_A$ receptor subtype, and is believed to represent almost half of all GABA$_A$ receptors in the brain.

Two other major populations are the α2βγ2 and α3βγ2/3 subtypes. Together these constitute approximately a further 35% of the total GABA$_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at α1βγ2, α2βγ2 or α3βγ2 subunits will possess desirable anxiolytic properties. The α1-selective GABA$_A$ receptor agonists alpidem and zolpidem are clinically prescribed as hypnotic agents, suggesting that at least some of the sedation associated with known anxiolytic drugs which act at the BZ1 binding site is mediated through GABA$_A$ receptors containing the α1 subunit. Accordingly, it is considered that GABA$_A$ receptor agonists which bind more effectively to the α2 and/or α3 subunit than to α1 will be effective in the treatment of anxiety with a reduced propensity to cause sedation. Also, agents which are antagonists or inverse agonists at α1 might be employed to reverse sedation or hypnosis caused by α1 agonists.

SUMMARY OF THE INVENTION

Compounds according to Formula (I) or a salt thereof are selective ligands for GABA$_A$ receptors useful for treatment of disorders of the central nervous system:

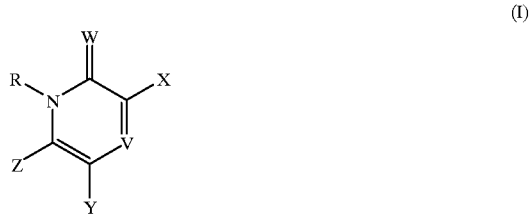

(I)

DETAILED DESCRIPTION OF THE INVENTION

The compounds of the present invention, being selective ligands for GABA$_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; and depressive or bipolar disorders, for example single-episode or recurrent major depressive disorder, dysthymic disorder, bipolar I and bipolar II manic disorders, and cyclothymic disorder.

The present invention provides a compound which is a derivative of formula I or a salt or prodrug thereof:

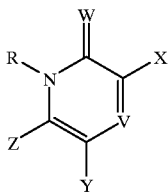

I wherein:
R is hydrogen, $C_{1-6}$ alkyl, $C_{2-6}$ alkenyl, $C_{2-6}$ alkynyl, $C_{1-6}$ alkoxy, $C_{2-6}$ alkenyloxy or $C_{2-6}$ alkynyloxy, and when R is not hydrogen, R is optionally independently substituted by one or more halogen atoms or hydroxy, cyano or amino groups;

V is CH or N;

W is O or S;

X is phenyl unsubstituted or substituted with one or more groups independently selected from $C_{1-6}$ alkyl, $CF_3$, cyano, nitro, halogen, amino, $C_{1-6}$ alkoxy, $C_{1-6}$ alkylcarbonyloxy or $C_{1-6}$ alkylcarbonylamino; a six-membered heteroaromatic group containing one or two nitrogen atoms or a five-membered heteroaromatic group containing one, two, three or four heteroatoms independently selected from N, O and S providing that not more than one heteroatom is selected from O and S, the heteroaromatic group being unsubstituted or substituted with one or more groups independently selected from halogen, $C_{1-6}$ alkyl, $C_{2-6}$ alkenyl, $C_{2-6}$ alkynyl, $C_{3-6}$ cycloalkyl, $C_{4-6}$ cycloalkenyl and $CF_3$;

Y is hydrogen, $NR^1R^2$, $C_{1-6}$ alkyl, $C_{2-6}$ alkenyl, $C_{2-6}$ alkynyl, Ar, $O(CH_2)_nAr^1$, $(CH_2)_jAr^2$, $C_kH_{2k-2}Ar^2$, $C_kH_{2k-4}Ar^2$ or $NH(CH_2)_lAr^5$;

$R^1$ and $R^2$ are independently selected from hydrogen, $C_{1-6}$ alkyl, $C_{2-6}$ alkenyl, $C_{2-6}$ alkynyl, $C_{1-6}$ hydroxyalkyl and $(CH_2)_mAr^3$;

Ar is thienyl, furyl or a six-membered heteroaromatic ring containing one or two nitrogen atoms which is unsubstituted or substituted with one or more groups independently selected from halogen and $C_{1-6}$ alkyl groups and which is optionally fused to a benzene ring; or naphthyl or phenyl rings which rings are unsubstituted or substituted with one or more groups independently selected from halogen, cyano, amino, nitro, $C_{1-6}$ alkyl, $C_{2-6}$ alkenyl, $C_{2-6}$ alkynyl, $CF_3$, $CF_3O$, $C_{1-6}$ alkoxy, $C_{2-6}$ alkenyloxy, $C_{2-6}$ alkynyloxy, $C_{1-6}$ alkylthio, $C_{2-6}$ alkenylthio, $C_{2-6}$ alkynylthio, hydroxy, hydroxy$C_{1-6}$alkyl, $NR^3R^4$, $OC(O)NR^3R^4$, $C_{1-6}$ alkoxyphenyl$C_{1-6}$alkoxy, cyano$C_{1-6}$alkyl, cyano$C_{2-6}$alkenyl, cyano$C_{2-6}$alkynyl, pyridyl, phenyl, $C_{1-6}$ alkoxycarbonyl, $C_{1-6}$ alkoxycarbonyl$C_{1-6}$alkyl, $C_{1-6}$ alkoxycarbonyl$C_{2-6}$alkenyl, $C_{1-6}$ alkoxycarbonyl$C_{2-6}$alkynyl and —$O(CH_2)_pO$— and which is optionally fused to a benzene ring;

$Ar^1$, $Ar^2$, $Ar^3$ and $Ar^5$ are independently selected from pyridyl; and phenyl which is unsubstituted or substituted with one or more groups independently selected from halogen, cyano, amino, nitro, $C_{1-6}$ alkyl, $C_{2-6}$ alkenyl, $C_{2-6}$ alkynyl, $CF_3$, $C_{1-6}$ alkoxy, $C_{2-6}$ alkenyloxy, $C_{2-6}$ alkynyloxy, $C_{1-6}$ alkylthio, $C_{2-6}$ alkenylthio, $C_{2-6}$ alkynylthio and —$O(CH_2)_pO$—;

Z is halogen, $C_{3-6}$ cycloalkyl, $C_{1-6}$ alkylthio, $C_{2-6}$ alkenylthio, $C_{2-6}$ alkynylthio, $NR^5R^6$, $Ar^4$ or $Het^1$;

$R^3$, $R^4$, $R^5$ and $R^6$ are independently as defined for $R_1$ and $R_2$;

$Ar^4$ is phenyl which is unsubstituted or substituted with one or more groups independently selected from halogen, cyano, amino, nitro, $C_{1-6}$ alkyl, $C_{2-6}$ alkenyl, $C_{2-6}$ alkynyl, $CF_3$, $C_{1-6}$ alkoxy, $C_{2-6}$ alkenyloxy, $C_{2-6}$ alkynyloxy, $C_{1-6}$ alkylthio, $C_{2-6}$ alkenylthio, $C_{2-6}$ alkynylthio and —$O(CH_2)_pO$—;

$Het^1$ is a four- or five-membered saturated ring containing a nitrogen atom optionally substituted by a hydroxy group; a six membered saturated ring containing a nitrogen atom, and optionally a further nitrogen atom or an oxygen atom; an unsaturated five-membered heterocyclic group containing one, two, three or four heteroatoms independently selected from N, O and S providing that not more than one heteroatom is selected from O and S; or an unsaturated six-membered heterocyclic group containing one or two nitrogen atoms; each of which moieties is unsubstituted or substituted by one or more groups independently selected from halogen, cyano, amino, $C_{1-6}$ alkyl, $C_{2-6}$ alkenyl, $C_{2-6}$ alkynyl, $CF_3$, $C_{1-6}$ alkoxy, $C_{2-6}$ alkenyloxy and $C_{2-6}$ alkynyloxy;

j is 1, 2, 3 or 4;

k is 2, 3 or 4;

l is 1, 2, 3 or 4;

m and n are independently 0, 1, 2, 3 or 4; and p is 1, 2 or 3.

R is preferably hydrogen, $C_{1-6}$ alkyl, $C_{2-6}$ alkenyl, $C_{2-6}$ alkynyl, $C_{1-6}$ alkoxy, $C_{2-6}$ alkenyloxy or $C_{2-6}$ alkynyloxy, in particular hydrogen, $C_{1-4}$ alkyl or $C_{2-4}$ alkenyl. When R is not hydrogen, R may be unsubstituted or substituted by one or two, preferably one, substituent independently selected from halogen, preferably fluorine or chlorine, especially fluorine, and hydroxy. In particular R can be hydrogen, methyl, n-propyl, ethenyl, prop-1-en-3-yl, hydroxyethyl or fluoroethyl.

V is generally CH. V may be N.

W is generally O. W may be S.

When X is phenyl it is preferably unsubstituted or substituted with $C_{1-6}$ alkyl, $CF_3$, cyano, nitro, halogen, amino, $C_{1-6}$ alkoxy, $C_{1-6}$ alkylcarbonyloxy or $C_{1-6}$ alkylcarbonylamino, for example, $C_{1-6}$ alkyl, amino, halogen or $C_{1-6}$ alkylcarbonylamino, more preferably unsubstituted or substituted with $C_{1-6}$ alkylcarbonylamino and most preferably unsubstituted or substituted with methylcarbonylamino.

When X is phenyl it may be unsubstituted. When X is phenyl it may be unsubstituted or substituted by fluorine, amino or methylcarbonylamino.

When X is a heteroaromatic group it is preferably unsubstituted or substituted with halogen, $C_{1-6}$ alkyl, $C_{2-6}$ alkenyl, $C_{2-6}$ alkynyl, $C_{3-6}$ cycloalkyl, $C_{4-6}$ cycloalkenyl or $CF_3$, more preferably unsubstituted or substituted with $C_{1-6}$ alkyl or $C_{3-6}$ cydoalkyl, most preferably unsubstituted or substituted with methyl or cyclopropyl. When X is a heteroaromatic group it may be unsubstituted or substituted by methyl, isopropyl, cyclopropyl, ethyl or chlorine.

When X is a heteroaromatic group it is preferably pyridyl or five-membered, in particular, an isothiazole, thiazole, pyrazolyl, thiadiazole oxadiazole, pyridine or thiophene, most preferably an isothiazol-5-yl group optionally substituted at the 3-position, a thiazol-2-yl group optionally substituted at the 4-position, a pyrazol-3-yl group optionally substituted at the 1-position, a thiadiazol-3-yl group, in particular 1,2,4-thiadiazol-3-yl group, optionally substituted at the 5-position, an oxadiazol-3-yl group, in particular a 1,2,4-oxadiazol-3-yl group, optionally substituted at the 5-position, a pyridin-2-yl group, a thien-2-yl group optionally substituted at the 4-position, a thien-3-yl group.

Y is preferably hydrogen, $NR^1R^2$, $C_{2-6}$ alkynyl, Ar, $O(CH_2)_nAr^1$ or $C_kH_{2k-4}A^2$.

$R^1$ and $R^2$ are preferably independently selected from $C_{1-6}$ alkyl and $(CH_2)_mAr^3$ and most preferably from methyl and $(CH_2)_mAr^3$.

When Ar is thienyl or furyl, thienyl is preferred, it is preferably unsubstituted or substituted with halogen or $C_{1-6}$ alkyl and optionally fused to a benzene ring and most preferably unsubstituted or fused to a benzene ring.

When Ar is a six-membered heteroaromatic ring it is preferably pyridyl or pyrimidinyl, and it is unsubstituted or substituted with halogen or $C_{1-6}$ alkyl and most preferably unsubstituted.

When Ar is naphthyl it is preferably unsubstituted and when phenyl it is preferably unsubstituted or substituted with $R^x$ and/or $R^y$ and/or $R^z$ wherein $R^x$ and $R^y$ are independently chosen from halogen, cyano, amino, nitro, $C_{1-6}$ alkyl, $C_{2-6}$ alkenyl, $C_{2-6}$ alkynyl, $CF_3$, $OCF_3$, $C_{1-6}$ alkoxy, $C_{2-6}$ alkenyloxy, $C_{2-6}$ alkynyloxy, $C_{1-6}$ alkylthio, $C_{2-6}$ alkenylthio, $C_{2-6}$ alkynylthio, hydroxy, hydroxy$C_{1-6}$alkyl, $NR^3R^4$, $OC(O)NR^3R^4$, $C_{1-6}$ alkoxyphenyl$C_{1-6}$alkoxy, cyano$C_{1-6}$alkyl, cyano$C_{2-6}$ alkenyl, cyano$C_{2-6}$ alkynyl, pyridyl, phenyl, $C_{1-6}$ alkoxycarbonyl, $C_{1-6}$ alkoxycarbonyl$C_{1-6}$alkyl, $C_{1-6}$ alkoxycarbonyl$C_{2-6}$alkenyl, $C_{1-6}$ alkoxycarbonyl$C_{2-6}$alkynyl and $-O(CH_2)_pO-$ and $R^z$ is halogen, $C_{1-6}$ alkyl or $C_{1-6}$ alkoxy and Ar is optionally fused to a benzene ring. More preferably, $R^x$ and $R^y$ are independently chosen from halogen, $C_{1-6}$ alkoxy, $-O(CH_2)_pO-$, hydroxy$C_{1-6}$alkyl, $C_{1-6}$ alkylthio, $C_{1-6}$ alkoxyphenyl$C_{1-6}$alkoxy, $NR^3R^4$, $OC(O)NR^3R^4$, cyano$C_{2-6}$alkenyl, pyridyl, $C_{1-6}$ alkoxycarbonyl, $C_{1-6}$ alkoxycarbonyl$C_{2-6}$ alkenyl, phenyl and $OCF_3$. Most preferably, when Ar is phenyl, it is unsubstituted and optionally fused to a benzene ring or substituted with one, two or three groups independently chosen from fluorine, chlorine, bromine, methoxy and methyl, or with $-O(CH_2)_pO-$, hydroxymethyl, ethoxy, isopropoxy, methoxyphenylmethoxy, $NR^3R^4$, $O(CO)NR^3R^4$, cyanoethenyl, pyridyl, ethoxycarbonyl, ethoxycarbonylethenyl, methylthio, phenyl, ethyl or $CF_3O$.

$Ar^1$, $Ar^2$, $Ar^3$ and $Ar^5$ are independently preferably pyridyl; or phenyl which is unsubstituted or substituted with halogen, cyano, amino, nitro, $C_{1-6}$ alkyl, $C_{2-6}$ alkenyl, $C_{2-6}$ alkynyl, $CF_3$, $C_{1-6}$ alkoxy, $C_{2-6}$ alkenyloxy, $C_{2-6}$ alkynyloxy, $C_{1-6}$ alkylthio, $C_{2-6}$ alkenylthio, $C_{2-6}$ alkynylthio or $-O(CH_2)_pO-$. More preferably when any of $Ar^1$, $Ar^2$, $Ar^3$ and $Ar^5$ are phenyl the one that is phenyl is unsubstituted or substituted with methyl.

$Ar^4$ is preferably phenyl which is unsubstituted or substituted with halogen, cyano, amino, nitro, $C_{1-6}$ alkyl, $C_{2-6}$ alkenyl, $C_{2-6}$ alkynyl, $CF_3$, $C_{1-6}$ alkoxy, $C_{2-6}$ alkenyloxy, $C_{2-6}$ alkynyloxy, $C_{1-6}$ alkylthio, $C_{2-6}$ alkenylthio, $C_{2-6}$ alkynylthio or $-O(CH_2)_pO-$ and most preferably unsubstituted phenyl.

Z is preferably chloro, $C_{3-6}$ cycloalkyl, $C_{1-6}$ alkylthio, $NR^5R^6$, $Ar^4$ or $Het^1$ and most preferably chloro, $C_{3-5}$ cycloalkyl, methylthio, $NR^5R^6$, $Ar^4$ or $Het^1$. When $Het^1$ is a saturated ring it is preferably unsubstituted or substituted with halogen, cyano, amino, $C_{1-6}$ alkyl, $C_{2-6}$ alkenyl, $C_{2-6}$ alkynyl, $CF_3$, $C_{1-6}$ alkoxy, $C_{2-6}$ alkenyloxy or $C_{2-6}$ alkynyloxy; more preferably it is a derivative of piperidine, thiomorpholine, azetidine, pyrrolidine or morpholine which derivative is preferably unsubstituted and which is preferably attached to the rest of the molecule via a nitrogen ring atom. When $Het^1$ is a derivative of pyrrolidine it may be unsubstituted or substituted by a hydroxy group.

When $Het^1$ is an unsaturated group it is preferably unsubstituted or substituted with halogen, cyano, amino, $C_{hd\ 1-6}$ alkyl, $C_{2-6}$ alkenyl, $C_{2-6}$ alkynyl, $CF_3$, $C_{1-6}$ alkoxy, $C_{2-6}$ alkenyloxy or $C_{2-6}$ alkynyloxy, more preferably it is unsubstituted or substituted with $C_{1-6}$ alkyl and most preferably it is unsubstituted or substituted with methyl. Preferably when $Het^1$ is an unsaturated group it is a derivative of furan, thiophene, imidazole, pyridine, pyrazine, pyrimidine or pyridazine. When Heti is furan it is preferably unsubstituted or substituted with $C_{1-6}$ alkyl, more preferably it is unsubstituted or substituted with methyl. When $Het^1$ is an unsaturated group it may be unsubstituted.

$R^3$ and $R^4$ are preferably independently $C_{1-6}$ alkyl and most preferably are both methyl.

$R^5$ and are preferably independently chosen from hydrogen and $C_{2-6}$ alkynyl, more preferably from hydrogen and propenyl and most preferably one is hydrogen and the other is propenyl.

j is preferably 1 or 2.

k is preferably 2.

l is preferably 1.

m and n are preferably 1.

p is preferably 1 or 2 and most preferably 2.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-6}$ alkoxy" and "$C_{1-4}$ alkyl" are to be construed accordingly.

The expression "$C_{2-6}$ alkenyl" includes ethenyl and straight-chained or branched propenyl, butenyl, pentenyl and hexenyl groups. Particular alkenyl groups are ethenyl, n-propenyl, isopropenyl and butenyl. Derived expressions such as "$C_{2-4}$ alkenyl" and "$C_{1-6}$ alkenyloxy" are to be construed accordingly.

The expression "$C_{2-6}$ alkynyl" includes ethynyl and propynyl groups and straight-chained or branched butynyl, pentynyl and hexynyl groups. Particular alkynyl groups are ethynyl, propynyl, butynyl and isobutynyl. Derived expressions such as "$C_{1-6}$ alkynyloxy" are to be construed accordingly.

Typical $C_{3-6}$ cycloalkyl groups include cyclopropyl, cyclobutyl, cyclopentyl and cyclohexyl. Derived expressions such as "$C_{3-5}$ cycloalkyl" are to be construed in an analogous manner.

The expressions "five-membered heteroaromatic group" and "unsaturated five-membered heterocyclic group" as used herein include furyl, thienyl, pyrrolyl, pyrazolyl, imidazolyl, triazolyl, tetrazolyl, oxadiazolyl, oxazolyl, isoxazolyl, thiazolyl, isothiazolyl and thiadiazolyl groups.

The expression "six-membered heteroaromatic ring" as used herein includes pyridyl, pyrazinyl, pyrimidinyl and pyridazinyl groups.

The expression "unsaturated six-membered heterocyclic group" as used herein includes pyridinyl, pyrimidinyl, pyridazinyl, pyrazinyl and triazinyl groups.

The term "halogen" as used herein includes fluorine, chlorine, bromine and iodine, especially fluorine or chlorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in uiuo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

The compounds of the present invention possess desirable binding properties at various $GABA_A$ receptor subtypes. The compounds in accordance with the present invention have good affinity as ligands for the α2 and/or α3 subunit of the human $GABA_A$ receptor. Typically, the compounds of this invention display more effective binding to the α2 and/or α3 subunit than to the α1 subunit. Typically, the compounds of the present invention have a binding affinity ($K_i$) for the subunit of 100 nM or less.

Specific compounds within the scope of the invention include:

3-(4-methoxyphenyl)-1-methyl-5-(thiazol-2-yl)-1H-[2,4'] bipyridinyl-6-one;

5-(4-methoxyphenyl)-1-methyl-6-(5-methylfuran-2-yl)-3-(3-methyl-[1,2,4]oxadiazol-5-yl)-1H-pyridin-2-one;

3-(4-methoxyphenyl)-1-methyl-5-(4-methylthiazol-2-yl)-1H-[2,4']bipyridinyl-6-one;

5-(4-methoxyphenyl)-1-methyl-3-(thiazol-2-yl)-6-(3-thienyl)-1H-pyridin-2-one;

5-(4-methoxyphenyl)-1-methyl-3-(5-cyclopropyl-[1,2,4]oxadiazol-3-yl)-6-(3-thienyl)-1H-pyridin-2-one;

5-(4-methoxyphenyl)-1-methyl-6-(5-methylfuran-2-yl)-3-(thiazol-2-yl)-1H-pyridin-2-one;

3-(4-methoxyphenyl)-1-methyl-5-(thiophen-2-yl)-1H-[2,4']bipyridinyl-6-one;

3-(4-methoxyphenyl)-1-methyl-5-(4-cyclopropylthiazol-2-yl)-1H-[2,4']bipyridinyl-6-one;

1-methyl-3-(4-pyridyl)-5-(thiazol-2-yl)-1H-[2,4']bipyridinyl-6-one;

3-(4-methoxyphenyl)-1-methyl-5-(4-methylthiophen-2-yl)-1H-[2,4']bipyridinyl-6-one;

5-(4-methoxyphenyl)-1-methyl-3-(4-methylthiazol-2-yl)-6-pyridazin-4-yl-1H-pyridin-2-one;

1-methyl-3-(4-methylthiazol-2-yl)-6-(pyridazin-4-yl)-5-(2,4,6-trifluorophenyl)-1H-pyridin-2-one;

5-benzyloxy-1-methyl-3-(4-methylthiazol-2-yl)-6-(pyridin-4-yl)-1H-pyridin-2-one;

5-benzyloxy-1-methyl-3-(4-methylthiazol-2-yl)-6-phenyl-1H-pyridin-2-one;

1-methyl-3-(1-methylpyrazol-3-yl)-5-(4-methoxyphenyl)-6-(pyridin-4-yl)-1H-pyridin-2-one;

5,6-diphenyl-1-methyl-3-(4-methylthiazol-2-yl)-1H-pyridin-2-one; 5-(3,4methylenedioxyphenyl)-1-methyl-3-(4-methylthiazol-2-yl)-6-(pyridin-4-yl)-1H-pyridin-2-one;

5-(4-methoxyphenyl)-1-methyl-3-(4-methylthiazol-2-yl)-6-(pyrazin-2-yl)-1H-pyridin-2-one;

5-(4-methoxyphenyl)-6-(4-pyridyl)-3-phenyl-1-methyl-1H-pyridin-2-one;

5-(4-methoxyphenyl)-3-(3-methylisothiazol-5-yl)-6-(4-pyridyl)-1-methyl-1H-pyridin-2-one;

1-methyl-3-(4-methylthiazol-2-yl)-5-(N-methyl-N-benzylamino)-6-(4-pyridyl)-1H-pyridin-2-one;

1-methyl-3,5-diphenyl-6-(4-pyridyl)-1H-pyrazin-2-one;

5-(4-methoxyphenyl)-1-methyl-3-(4-methylthiazol-2-yl)-6-(4-morpholino)-1H-pyridin-2-one;

6-dimethylamino-5-(4-Methoxyphenyl)-1-methyl-3-(4-methylthiazol-2-yl)-1H-pyridin-2-one;

1-methyl-3-(4-methylthiazol-2-yl)-6-(4-morpholino)-1H-[3,4']bipyridin-2-one;

1-methyl-3-(4-methylthiazol-2-yl)-6-(1-pyrrolidino)-1H-[3,4']bipyridin-2-one;

and salts and prodrugs thereof.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The present invention also provides a compound of formula I for use in a method of treatment of the human or animal body, in particular for use in the treatment of anxiety.

The present invention further provides the use of a compound of formula I for the manufacture of a medicament for the treatment of disorders for which the administration of a ligand for the $GABA_A$ receptor $\alpha 2$ and/or $\alpha 3$ subunits is required, for example, for the treatment of anxiety.

There is also disclosed a prophylactic or therapeutic method of treatment of a subject suffering from a condition for which the administration of a ligand for the $GABA_A$ receptor $\alpha 2$ andlor $\alpha 3$ subunit is required, which comprises administering to that subject a prophylactically or therapeutically effective amount of a compound of formula I. An example of such a condition is anxiety.

The present invention also provides a process for producing a compound of formula I in which V is CH which comprises:

(a) Reacting a compound of formula II with a compound of formula III

GCOJ                       (II)

YCH$_2$CO$_2$R'             (III)

wherein Y is as defined above, G is Z, or when Z is a nucleophile, G optionally represents a leaving group such as methoxy, R' is a leaving group such as $C_{1-6}$ alkyl, $C_{2-6}$ alkenyl or $C_{2-6}$ alkynyl which is unsubstituted or substituted with one or more halogen atoms and is typically $C_{1-6}$ alkyl such as methyl or tertiary butyl and J is hydroxy or a halogen atom, preferably hydroxyl, to give a compound of formula IV:

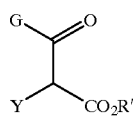

(IV)

wherein G, R' and Y are as defined above.

The compound of formula II is typically activated before reaction, for example, by reacting with N, N-carbonydiimidazole in a suitable solvent such as dry tetrahydrofuran. The compound of formula III is optionally converted into its enolate before reaction by reacting with a strong base such as lithium diisopropylamide in a suitable solvent such as dry tetrahydrofuran optionally with cooling, typically to $-78°$ C.

Activated compound II is typically reacted without purification as is the compound of formula III when activated.

When the compound of formula III is activated, reaction with the compound of formula II is typically carried out with cooling generally to $-78°$ C. When the compound of formula III is not activated it is typically reacted with the compound of formula II with cooling, generally to $-30°$ C., and with a strong base, such as sodium hydride; the reaction mixture is generally stirred for about one hour and then allowed to warm gradually to room temperature typically for about eight hours.

(b) Converting the compound of formula IV into a compound of formula V:

(V)

wherein G and Y are as defined above, which is achieved typically at room temperature or with heating, for example to $150°$ C., for from 2 to 18 hours, in a solvent such as dimethyl sulfoxide, generally in the presence of a salt such as sodium chloride and water; or in the presence of an acid such as trifluoracetic acid.

Alternatively, a compound of formula (V) in which Y is $NR^1R^2$, G is Z and $R^1$ and $R^2$ are as defined above, can be obtained by reacting a compound of formula $HNR^1R^2$ with a compound of formula XIX:

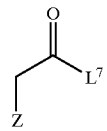

(XIX)

wherein Z is as defined above and $L^7$ is a leaving group such as a halogen, e.g. bromine, typically in the form of the hydrohalide. The reaction is typically carried out in a solvent such as dichloromethane at about room temperature for about 18 hours.

(c) Reacting the compound of formula V with a compound of formula VI:

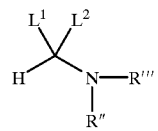

(VI)

wherein R" and R'" are independently hydrogen or $C_{1-6}$ alkyl, such as methyl, and $L^1$ and $L^2$ are leaving groups such as $C_{1-6}$ alkoxy, typically methoxy, to give a compound of formula VII:

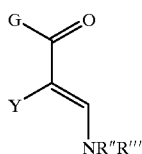

(VII)

wherein G, R", R'" and Y are as defined above.

The reaction is typically carried out in a solvent such as dimethyl-formamide at room temperature or at an elevated temperature such as 80° C. for from 3 to 20 hours.

(d) Reacting the compound of formula VII with a compound of formula VIII:

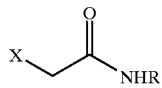

(VIII)

wherein X and R are as defined above, to give a compound of formula I':

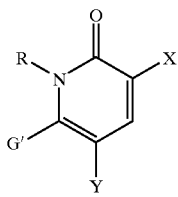

(I')

wherein R, X and Y are as defined above and when G was Z, G' is Z and when G was a leaving group, G' is hydroxy, i.e. when G' is Z the compound of formula I' is a compound of formula I in which V is CH.

The reaction is typically carried out under an inert atmosphere, such as nitrogen, in the presence of a small quantity of a protic solvent such as methanol, with a strong base, such as sodium hydride, in a solvent such as tetrahydrofuran or dimethylformamide, at from room temperature to 50° C. for from 15 to 20 hours.

(e) When $G^1$ is OH, reacting with halogenating agent such as $POCl_3$ to obtain a compound of formula I":

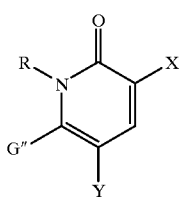

(I")

wherein R, X and Y are as defined above and G" is halogen, for example chlorine. This reaction is generally carried out under reflux under an inert atmosphere such as nitrogen for about one and a half hours.

(f) Reacting the compound of formula I" with a compound of formula Z—H, wherein Z is as defined above, generally in a solvent such as DMSO, typically at about 100° C. for about 18 hours, to obtain a compound of formula I in which Z is a nucleophile and V is CH.

In an alternative process, a compound of formula I in which V is CH is produced by a process comprising:

(a) Reacting a compound of formula V with a compound of formula IX:

NHR       (IX)

to give a compound of formula X:

(X)

wherein R, Y and Z are as defined above.

The reaction is typically carried out in a solvent such as chloroform, under an inert atmosphere, such as nitrogen, with cooling, for example to 0°C., with a catalyst, such as titanium tetrachloride, for from 5 to 10 hours.

(b) Reacting the compound of formula X with a compound of formula XI:

(XI)

wherein $L^4$ is a leaving group such as chlorine and P is a protecting group such as benzyl, to give a compound of formula XII:

(XII)

wherein P, $L^5$, R, Y and Z are as defined above.

The reaction is typically carried out in a solvent, such as dry tetrahydrofuran, at a reduced temperature, such as −78° C., under an inert atmosphere such as nitrogen followed by warming, typically to 0° C., for from 1 to 3 hours.

(c) Reacting the compound of formula XII in a Vilsmeier reaction, typically using $POCl_3$ and dimethylformamide, to give a compound of formula XIII:

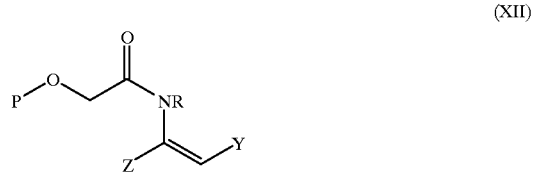

(XIII)

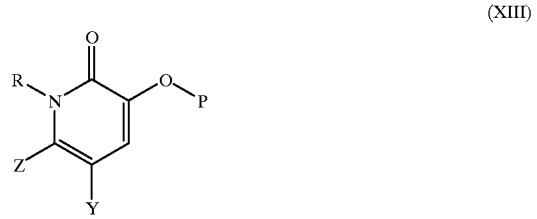

wherein R, P, Y and Z are as defined above.

The reaction is generally carried out by adding $POCl_3$ to the compound of formula XII at about room temperature and allowing the reaction to proceed for about an hour. DMF is then generally added, typically with cooling to about 0° C.

following by heating to about 75° C. for about 90 minutes. This is typically followed by further cooling to about 0° C. and the addition of further dimethylformamide followed by heating to about 75° C. for about 3 hours.

(d) Deprotecting the compound of formula XIII to obtain a compound of formula XIV:

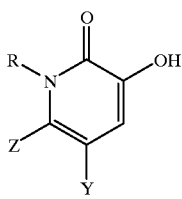

(XIV)

wherein R, Y and Z are as defined above, typically by reacting in a transfer dehydrogenation reaction, for example using palladium on carbon, in the presence of a hydrogen source such as ammonium formate, an acid such as glacial acetic acid and in a solvent such as methanol for about 3.5 hours at about room temperature.

(e) Converting the hydroxy group in the compound of formula XIV into a leaving group by reaction with an acid derivative of formula XV:

$$L^6-K \quad \quad (XV)$$

wherein K is an acyl or sulfonyl group, such as $SO_2CF_3$, and $L^6$ is a leaving group such as $OSO_2CF_3$, to give a compound of formula XVI:

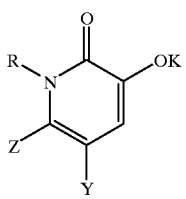

(XVI)

wherein K, R, Y and Z are as defined above.

The reaction is generally carried out in a solvent such as dry dichloromethane in the presence of a base such as pyridine generally with cooling to about −78° C. and for about one hour.

(f) Reacting the compound of formula XVI with a compound of XVII:

$$X-B(OH)_2 \quad \quad (XVII)$$

wherein X is as defined above, to obtain a compound of formula I. The reaction is carried out in the presence of a transition metal catalyst such as $Pd(PPh_3)_4$ generally under an inert atmosphere, such as nitrogen, typically at reflux, for about two hours.

Compounds of formula XVII can be made by reacting a compound of formula XVIII:

$$X-H \quad \quad (XVIII)$$

wherein X is as defined above, with a trialkylborate, such as trimethylborate, in the presence of a strong base, such as n-butyllithium, generally at room temperature for about two hours.

Compounds of formula XVIII are commercially available or can be made by known methods.

Where they are not commercially available, the starting materials of formulae II, III, $HNR^1R^2$, XIX, VI, VIII, IX, Z—H, XI and XV may be prepared by standard methods well known from the art.

Compounds of formula I in which W is S can be prepared by reacting the analagous compound in which W is O with Lawesson's reagent or $P_2S_5$.

Compounds of formula I in which V is N can be prepared by reacting a compound of formula:

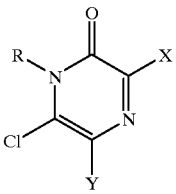

(XIX)

with Z-boronic acid (XX) wherein R, X, Y and Z are as previously defined. The compound of formula XX is generally in the form of a salt, such as the lithium salt. The reaction is generally carried out under an inert atmosphere such as nitrogen and in a solvent such as 3:1 ethylene glycol dimethylether:water. Generally addition of the compound of formula XX to the compound of formula XIX is followed by addition of a salt, such as sodium carbonate, and then a catalyst, such as tetrakistriphenylphosphine palladium. The order in which these compounds are combined is not critical. The reaction is generally carried out at reflux for several hours.

The compound of formula XIX can be prepared by reacting a compound of formula:

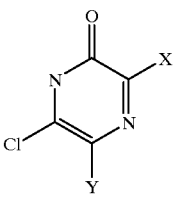

(XXI)

with a compound of formula:

$$Li-R \quad \quad (XXII)$$

wherein R, X and Y are as previously defined. The reaction is generally preceded by addition of a strong base, such as NaH, to the compound of formula XXI generally at 0° C. under an inert atmosphere such as nitrogen in a solvent such as 4:1 ethylene glycol dimethylether:dimethylformamide for about 5 minutes. The reaction between the compounds of formulae XXI and XXII is then carried out for several hours.

Compounds of formula XXI can be prepared by methods analagous to that disclosed in Cheeseman et al., *J. Chem. Soc. Chem. Commun.* 1971, (18), 2977–2979 from known starting materials which are either commercially available or can be made by standard methods well known in the art.

Compounds of formula XX and XXII are either commercially available or can be made by standard techniques well known in the art.

Compounds of formula I" constitute a further feature of the present invention as they act as ligands of $GABA_A$ receptors containing the α2 and/or α3 subunits. Preferred substitution patterns of these compounds are the same as for the compounds of formula I mutatis mutandis.

It will be understood that any compound of formula I initially obtained from any of the above processes may, where appropriate, subsequently be elaborated into a further compound of formula I by techniques known from the art.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

EXAMPLE 1

3-(4-Methoxyphenyl)-1-methyl-5-(thiazol-2-yl)-1H-[2,4']bipyridinyl-6-one

Step 1: N,N-Carbonyldiimidazole (20.3 g) was added portionwise to a stirred suspension of isonicotinic acid (15.4 g) in dry tetrahydrofuran (200 cm$^3$). The gently effervescent mixture was stirred at room temperature for 90 minutes, forming an orange solution. A solution of lithium diisopropylamide was prepared by the addition of n-butyllithium (2.5 M, hexanes; 100 cm$^3$) to a stirred solution of diisopropylamine (35 cm$^3$) in dry tetrahydrofuran (250 cm$^3$) at 0° C. under nitrogen. The solution was cooled to −78° C. for 15 minutes, followed by the dropwise addition of a solution of methyl 2-(4-methoxyphenyl)acetate (45 g) in dry tetrahydrofuran (50 cm$^3$) at −78° C. The yellow enolate solution was stirred at −78° C. for 20 minutes, followed by addition of the imidazolide solution dropwise via cannula. After stirring at −78° C. for 45 minutes the bright yellow suspension was warmed to room temperature. The mixture was poured into aqueous hydrochloric acid (1.3 M; 700 cm$^3$) and washed with hexane (200 cm$^3$). The aqueous solution was basified to pH 3 with aqueous sodium hydroxide (4 M) and then to pH 7 with saturated aqueous sodium hydrogencarbonate. The neutralised solution was extracted with dichloromethane (2×400 cm$^3$). The organic extracts were washed with brine (300 cm$^3$), dried (magnesium sulphate), filtered and concentrated to give a brown oil that crystallised on standing. The material was triturated with ethyl acetate-diethyl ether (1:1; 50 cm$^3$) and filtered to give 2-(4-methoxyphenyl)-3-oxo-3-(pyridin-4-yl)propionic acid methyl ester as an off-white solid (14.7 g; 42%). $\delta_H$ (250 MHz; CDCl$_3$) 3.77 (3 H, s, OCH$_3$), 3.79 (3 H, s, OCH$_3$), 5.48 (1 H, s, MeO$_2$CCH), 6.90 (2 H, d, J 9, methoxyphenyl H-2), 7.28 (2 H, d, J 9, methoxyphenyl H-3), 7.70 (2 H, d, J 6, pyridyl H-3) and 8.77 (2 H, d, J 6, pyridyl H-2).

Step 2: A mixture of 2-(4-methoxyphenyl)-3-oxo-3-(pyridin-4-yl)propionic acid methyl ester (14.7 g), sodium chloride (6.0 g) and water (1.9 cm$^3$) in dimethyl sulphoxide (200 cm$^3$) was stirred at 150° C. for 2 hours. The solution was cooled to room temperature, poured into water (600 cm$^3$) and extracted with ethyl acetate-diethyl ether (1:1; 2×400 cm$^3$). The extracts were dried (magnesium sulphate), filtered and concentrated to give 2-(4-methoxyphenyl)-1-(pyridin-4-yl)ethanone as a brown solid (10.2 g; 87%). $\delta_H$ (250 MHz; CDCl$_3$) 3.79 (3 H, s, OCH$_3$), 4.44 [2 H, s, C(O)CH$_2$Ar], 6.88 (2 H, d, J 9, methoxyphenyl H-2), 7.16 (2 H, d, J 9, methoxyphenyl H-3), 7.77 (2 H, d, J 6, pyridyl H-3) and 8.80 (2 H, d, J 6, pyridyl H-2).

Step 3: A solution of 2-(4-methoxyphenyl)-1-(pyridin-4-yl)ethanone (10.2 g) and dimethylformamide-dimethylacetal (20 cm3) in dry dimethylformamide (50 cm$^3$) was stirred at 80° C. for 4 hours. The mixture was cooled, poured into water (500 cm$^3$) and extracted with ethyl acetate (3×200 cm$^3$). The combined extracts were washed with brine (100 cm$^3$), dried (magnesium sulphate), filtered and concentrated to give a yellow solid. The material was washed well with diethyl ether-hexane (1:9; 2×100 cm$^3$) and dried in vacuo to give 3-dimethylamino-2-(4-methoxyphenyl)-1-(pyridin-4-yl)propen-1-one as a beige solid (7.7 g; 60%). $\delta_H$ (250 MHz; CDCl$_3$) 2.78 [6 H, broad s, N(CH$_3$)$_2$], 3.79 (3 H, s, OCH$_3$), 6.79 (2 H, d, J 9, methoxyphenyl H-2), 7.04 (2 H, d, J 9, methoxyphenyl H-3), 7.24 (2 H, d, J 6, pyridyl H-3) 7.40 (1 H, s, C=CH) and 8.51 (2 H, d, J 6, pyridyl H-2).

Step 4: A solution of 3-dimethylamino-2-(4-methoxyphenyl)-1-(pyridin-4-yl)propen-1-one (2.53 g), N-methyl thiazol-2-ylacetamide (1.70 g) and methanol (0.73 cm$^3$) in dry dimethylformamide (20 cm$^3$) was added via cannula at room temperature to a stirred suspension of sodium hydride (55% in oil; 0.80 g) in dry dimethylformamide (10 cm$^3$) under nitrogen. The mixture was stirred at 40° C. for 18 hours, then poured into water (200 cm$^3$). The resulting yellow precipitate was collected and recrystallised from ethyl acetate to give 3-(4-methoxyphenyl)-1-methyl-5-(thiazol-2-yl)-1H-[2,4']bipyridinyl-6-one as a yellow powder (2.18 g; 62%) m.p. 224–225° C. (EtOAc). Found: C, 66.9; H, 4.45; N, 11.2. C$_{12}$H$_{17}$N$_3$O$_2$S requires C, 67.2; H, 4.6; N, 11.2%. $\delta_H$ (360 MHz; CDCl$_3$) 3.50 (3 H, s, NCH$_3$), 3.74 (3 H, s, OCH$_3$), 6.70 (2 H, d, J 9, methoxyphenyl H-2), 6.93 (2 H, d, J 9, methoxyphenyl H-3), 7.15 (2 H, d, J 6, pyridyl H-3), 7.50 (1 H, d, J 3, thiazolyl H-5), 7.96 (1 H, d, J 3, thiazolyl H-4), 8.64 (2 H, d, J 6, pyridyl H-2) and 8.72 (1 H, s, pyridone H-4); m/z (ESP+) 376 (MH$^+$; 100%).

EXAMPLE 2

5-(4-Methoxyphenyl)-1-methyl-6-(5-methylfuran-2-yl)-3-(3-methyl-[1,2 4]oxadiazol-5-yl)-H-Pyridin-2-one Preparation of this compound was carried out as described for Example 1 replacing isonicotinic acid with 5-methylfuran-2-carboxylic acid in Step 1 and N-methyl-thiazol-2-ylacetamide with N-methyl 3-methyl[1.2.4]oxadiazol-5-ylacetamide in Step 4. Yellow solid m.p. 179° C.; (Found: C, 67.03; H, 5.06; N, 10.87. C$_{21}$H$_{19}$N$_3$O$_4$ requires C, 66.83; H, 5.07; N, 11.13%); $\delta_H$(360 MHz; CDCl$_3$) 2.33 (3 H, s, furan-Me), 2.48 (3 H, s, oxadiazole-Me), 3.57 (3 H, s, NMe), 3.79 (3 H, s, OMe), 5.96 (1 H, d, J 4, furan4-H), 6.02 (1 H, d, J 4, furan H-3), 6.80 (2 H, d, J 9, ArH o to OMe), 6.97 (2 H, d, J9, ArH m to OMe), 8.35 (1 H, s, pyridone H-4); m/z (ES)378 (MH$^+$,100%).

EXAMPLE 3

3-(4-Methoxyphenyl)-1-methyl-5-(4-methylthiazol-2-yl)-1H-[2,4']bipyridinyl-6-one Preparation of this compound was carried out as described for Example 1 replacing N-methyl thiazol-2-ylacetamide with N-methyl 4-methylthiazol- 2-ylacetamide in Step 4. Lemon yellow prisms m.p. 228–230° C. (EtOAc). Found: C, 68.1; H, 4.7; N, 10.7. $C_{22}H_{19}N_3O_2S$ requires C, 67.9; H, 4.9; N, 10.8% $\delta_H$ (360 MHz; CDCl$_3$) 2.58 (3 H, s, ArCH$_3$), 3.48 (3 H, s, NCH$_3$), 3.74 (3 H, s, OCH$_3$), 6.70 (2 H, d, J 9, methoxyphenyl H-2), 6.95(2 H, d, J9, methoxyphenyl H-3), 7.08 (1 H, s, thiazolyl H-3), 7.15 (2 H, d, J 6, pyridyl H-3) 8.65 (2 H, d, J 6, pyridyl H-2) and 8.90 (1 H, broad s, pyridone H-4); m/z (ESP+) 390 (MH$^+$; 100%).

EXAMPLE 4

5-(4-Methoxyphenyl)-1-methyl-3-(thiazol-2-yl)-6-(3-thienyl)-1H-pyridin-2-one

Preparation of this compound was carried out as described for Example 1 replacing isonicotinic acid with thiophene-3-carboxylic acid in Step 1. Yellow needles m.p. 185–187° C. (EtOAc/hexanes)(Found: C, 63.38; H, 3.99; N, 7.54. $C_{20}H_{16}N_2O_2S_2$ requires C, 63.14; H, 4.24; N, 7.36%); $\delta_H$ (360 MHz, d$_6$-DMSO) 3.42 (3 H, s, NMe), 3.71 (3 H, s, OMe), 6.79 (2 H, d, J 9, methoxyphenyl H-2), 7.02 (2 H, d, J 9, methoxyphenyl H-3), 7.54 (1 H, dd, J 1 and 4, thiophene-H), 7.55 (1 H, dd, J 1 and 3, thlophene-H), 7.64 (1 H, dd, J 3 and 4, thiophene-H), 7.77 (1 H, d, J 3.3, thiazole-H), 7.95 (1 H, d, J 3.3, thiazole-H), 8.47 (1 H, s, pyridone H-4); m/z (ESP+) 381 (MH$^+$).

EXAMPLE 5

5-(4-Methoxyphenyl)-1-methyl-3-(5-cyclopropyl-[1,2,4]oxadiazol-3-yl)-6-(3-thienyl)-1H-,pyrdin-2-one Preparation of this compound was carried out as described for Example 1 replacing isonicotinic acid with thiophene-3-carboxylic acid in Step 1 and N-methyl thiazol-2-ylacetamide with N-methyl 5-cyclopropyl[1.2.4]oxadiazol-3-ylacetamide in Step 4. Yellow needles m.p. 171–173° C. (EtOAc/hexanes)(Found: C, 65.33; H, 4.42; N, 10.37. $C_{22}H_{19}N_5O_3S$ requires C, 65.17; H, 4.72; N, 10.36%); $\delta_H$ (360 MHz, d$_6$-DMSO) 1.1–1.2 (2 H, m, CH$_2$), 1.2–1.3 (2 H, m, CH$_2$),2.3–2.4 (1 H, m, cyclopropyl-H), 3.26 (3 H, s, NMe), 3.70 (3 H, s, OMe), 6.79 (2 H, d, J 9, methoxyphenyl H-2), 7.06 (2 H, d, J9, methoxyphenyl H-3), 7.10 (1 H, dd, J 3 and 4, thiophene-H ), 7.28 (1 H, dd, J 1 and 3, thiophene-H), 7.70 (1 H, dd, J 1 and 4, thiophene-H), 8.07 (1 H, s, pyridone H-4); m/z (ESP+) 406 (MH$^+$).

EXAMPLE 6

5-(4-Methoxyphenyl)-1 -methyl-6-(5-methylfuran-2-yl)-3-(thiazol-2-yl)-1H-pyridin-2-one Preparation of this compound was carried out as described for Example 1 replacing isonicotinic acid with 5-methylfuran-2-carboxylic acid in Step 1. Orange rhombs m.p. 205–206° C. (EtOAc/hexanes)(Found: C, 66.95; H, 4.71; N, 7.38. $C_{21}H_{18}N_2O_3S$ requires C, 66.65; H, 4.79; N, 7.40%); $\delta_H$ (360 MHz, d$_6$-DMSO) 2.27 (3 H, s, furan-Me), 3.49 (3 H, s, NMe), 3.74 (3 H, s, OMe), 6.16 (1 H, d, J 3.2, furan-H), 6.34 (1 H, d, J3.2 furan-H), 6.87 (2 H, d, J 8.8, ArH o to OMe), 7.05 (2 H, d, J 8.8, ArH m to OMe), 7.80 (1 H, d, J 3.2, thiazole-H), 7.98 (1 H, d, J 3.2, thiazole-H), 8.48 (1 H, s, pyridone H-4); m/z (ESP+) 379 (MH$^+$).

EXAMPLE 7

3-(4-Methoxyphenyl)-1-methyl-5-(thiophen-2-yl)-1H-[2,47']bipyridinyl-6-one

Preparation of this compound was carried out as described for Example 1 replacing N-methyl thiazol-2-ylacetamide with N-methyl thien-2-ylacetamide in Step 4. Beige prisms mn.p. 213–214° C. (EtOAc)(Found: C, 70.3; H, 5.0; N, 7.5. $C_{22}H_{18}N_2O_2S$ requires C, 70.6; H, 4.9; N, 7.5%); $\delta_H$ (360 MHz; CDCl$_3$) 3.45 (3 H, s, NCH$_3$), 3.75 (3 H, s, OCH$_3$), 6.72 (2 H, d, J 9, methoxyphenyl H-2), 6.91 (2 H, d, J 9, methoxyphenyl H-3), 7.12 (1 H, dd, J5 and 4, thiophene H-4), 7.17 (2 H, broad m, pyridyl H-3), 7.41 (1 H, dd, J 5 and 1, thiophene H-3), 7.70 (1 H, dd, J 4 and 1, thiophene H-6), 7.90 (1 H, s, pyridone H-4) and 8.64 (2 H, broad in, pyridyl H-2); m/z (ESP+) 375 (MH$^+$; 100%).

EXAMPLE 8

3-(4-Methoxyphenyl)-1 -methyl-5-(4-cyclopropylthiazol-2-yl)-1H-[2,4']bipyridinyl-6-one Preparation of this compound was carried out as described for Example 1 replacing N-methyl thiazol-2-ylacetamide with N-methyl 4-cyclopropylthiazol-2-ylacetamide in Step 4. Bright yellow prisms m.p. 211–213° C. (EtOAc)(Found: C, 67.5; H, 5.4; N, 10.1. $C_{24}H_{21}N_3O_2S.0.6(H_2O)$ requires C, 67.6; H, 5.3; N, 9.9%); $\delta_H$ (360 MHz; CDCl$_3$) 0.90–1.02 (4 H, m, cyclopropyl CH$_2$), 2.18–2.24 (1 H, m, cyclopropyl CH), 3.48 (3 H, s, NCH$_3$), 3.75 (3 H, s, OCH$_3$), 6.72 (2 H, d, J 9, methoxyphenyl H-2), 6.94 (2 H, d, J 9, methoxyphenyl H-3), 6.98 (1 H, s, thiazolyl H-5), 7.16 (2 H, d, J6, pyridyl H-3), 8.64 (2 H, d, J6, pyridyl H-2) and 8.76 (1 H, broad s, pyridone H-4); 7m/z (ESP+) 416 (MH$^+$; 100%).

EXAMPLE 9

1-Methyl-3-(4-pyridyl)-5-(thiazol-2-yl)-1H-[2,4']bipyridinyl-6-one

Preparation of this compound was carried out as described for Example 1 replacing methyl 2-(4-methoxyphenyl) acetate with methyl 4-pyridylacetate in Step 4. Yellow needles m.p. 251–253° C. (CHCl$_3$/hexanes)(Found: C, 64.85; H, 3.96; N, 15.53. $C_{19}H_{14}N_4O_3+0.3 H_2O$ requires C, 64.88; H, 4.18; N, 15.93%); $\delta_H$ (360 MHz, d$_6$-DMSO) 3.37 (3 H, s, NMe), 7.11 (2 H, d, J 4.5, pyridyl-H), 7.46 (2 H, d, J 4.5 pyridyl-H), 7.82 (1 H, d, J 3.2, thiazole-H), 8.00 (1 H, d, J 3.2, thiazole-H), 8.41 (2 H, d, J 4.5, pyridyl-H), 8.52 (1 H, s, pyridone H-4), 8.65 (2 H, d, J 4.5, pyridyl-H); m/z (ESP+) 347 (MH$^+$).

EXAMPLE 10

3-(4-Methoxyphenyl)-1-methyl-5-(4-methylthiophen-2-yl)-1H-[2,4']bipyridinyl-6-one Preparation of this compound was carried out as described for Example 1 replacing N-methyl thiazol-2-ylacetamide with N-methyl 4-methylthien-2-ylacetamide in Step 4. Lemon yellow prisms m.p. 169–170° C. (EtOAc). Found: C, 71.4; H, 5.0; N, 7.3. $C_{23}H_{20}N_2O_2S$ requires C, 71.1; H, 5.2; N, 7.2%. $\delta_H$ (360 MHz; CDCl$_3$) 2.30 (3 H, s, ArCH$_3$), 3.453

(3 H, s, NCH₃), 3.75 (3 H, s, OCH₃), 6.71 (2 H, d, J 9, methoxyphenyl H-2), 6.90 (2 H, d, J 9, methoxyphenyl H-3), 7.00 (1 H, s, thiophene H-3), 7.11 (2 H, d, J 6, pyridyl H-3), 7.56 (1 H, s, thiophene H-5), 7.85 (1 H, s, pyridone H-4) and 8.60 (2 H, d, J6, pyridyl H-2); m/z (ESP+) 389 (MH+; 100%).

EXAMPLE 11

5-(4-Methoxyphenyl)-1-methyl-3-(4-methylthiazol-2-yl)-6-Dyridazin-4-yl-1H-pyridin-2-one Preparation of this compound was carried out as described for Example 1 replacing isonicotinic acid with pyridazin-4-carboxylic acid in Step 1 and N-methyl thiazol-2-ylacetamide with N-methyl 4-methylthiazol-2-ylacetamide in Step 4. M.p. 271° C.; (Found: C, 64.86; H, 4.51; N, 14.21. $C_{21}H_{18}N_4O_2S$ requires C, 64.59; H, 4.65; N, 14.35%); $\delta_H$ (360 MHz; CDCl₃) 2.51 (3 H, s, thiazole-Me), 3.50 (3 H, s, NMe), 3.74 (3 H, s, OMe), 6.71 (2 H, d, J 9, methoxyphenyl H-2), 6.89 (2 H, d, J 9, methoxyphenyl H-3), 7.08 (1 H, s, thiazole 5-H), 7.27 (1 H, dd, J 1 and 8, pyridazine 5-H), 8.66 (1 H, s, pyridone H-4), 9.06 (1 H, d, J 1, pyridazine 3-H), 9.20 (1 H, dd, J 1 and 8, pyridazine 6-H); m/z 391 (M+, 100%).

The following compounds were prepared in a similar manner using analogous starting materials:

EXAMPLE 12

1-Methyl-3-(4-methylthiazol-2-yl)-6-(pyridazin-4-yl)-5-(2,4,6-trifluorophenyl)-1H-pyridin-2-one.

$\delta_H$ (250 MHz; CDCl₃); 2.52 (3H, s), 3.50 (3H, s), 6.58 (2H, m), 7.1 (1H, s), 7.38 (1H, m), 8.52 (1H, s), 9.1 (1H, s), and 9.28 (1H, dd, J 1.2 and 5.3Hz); m/z (ESP+) 415 (MH+).

EXAMPLE 13

5-Benzyloxy-1-methyl-3-(4-methylthiazol-2-yl)-6-(pyridin-4-yl)-1H-pyridin-2-one.

$\delta_H$ (250 MHz; CDCl₃) 2.56 (3 H, apparent d, J 0.7, thiazole-CH₃), 3.41 (3 H, s, CH₃N), 5.05 (2 H, s, PhCH₂O), 6.97 (1 H, d, J 2.4, phenyl), 6.99 (1 H, d, J 1.6, phenyl), 7.11–7.07 (3 H, m, aromatic), 7.29–7.20 (3 H, aromatic), 8.74–8.72 (3 H, m, pyridone-H and pyridyl-H).

EXAMPLE 14

5-Benzyloxy-1-Methyl-3-(4-methylthiazol-2-yl)-6-(phenyl)-1H-pyridin-2-one.

$\delta_H$ (360 MHz; CDCl₃) 2.55 (3 H, apparent d, J 0.6, thiazole-CH₃), 3.44 (3 H, s, CH₃N), 4.82 (2 H, s, PhC H₂O), 6.96 (1 H, d, J 2.5, phenyl), 6.97 (1H, d, J 1.6, phenyl), 7.03 (1 H, apparent d, J 0.6, thiazole-H), 7.25–7.18 (5 H, m, phenyl), 7.50–7.46 (3 H, m, phenyl), 8.72 (1 H, s, pyridone-H).

EXAMPLE 15

1-Methyl-3-(1-methylpyrazol-3-yl)-5-(4-methoxyphenyl)-6-(pyridin-4-yl)-1H-pyridin-2-one.

$\delta_H$ (360 MHz; CDCl₃) 3.41 (3 H, s, NCH₃), 3.73 (3 H, s, OCH₃), 3.95 (3H, Pyrazole-N-Me), 6.67 (2 H, d, J 9, methoxyphenyl H-2)), 6.90 (2 H, d, J 9, methoxyphenyl H-3), 7.11 (2 H, d, J 6, pyridyl H-3), 7.26 (1 H, d, J 3, Pyrazole H-4), 7.42 (1 H, d, J 3, Pyrazole H-4), 8.22 (1 H, s, pyridone CH), 8.6 (2 H, d, J 6, pyridyl H-2)

EXAMPLE 16

5,6-Diphenyl-1-Methyl-3-(4-mothylthiazol-2-yl)1H-pyridin-2-one.

$\delta_H$ (360 MHz; CDCl₃) 2.51 (3 H, s, thiazole-CH₃), 3.50 (3 H, s, CH₃N), 7.03–7.01 (3 H, m, phenyl), 7.18–7.12 (5 H, m, phenyl), 7.34–7.32 (3 H, m, phenyl), 8.70 (1 H, s, pyridone-H).

EXAMPLE 17

5-(3,4-Methylenedioxyphenyl)-1-methy-3-(4-methylthiazol-2-yl)-6-pyridin-4-yl)-1H-pyridin-2-one.

$\delta_H$ (360 MHz; CDCl₃) 2.51 (3 H,s, CH₃), 3.47 (3 H, s, NCH₃), 4.19 (4 H, S, CH₂CH₂), 6.43(1 H, dd, J 2,8, benzodioxan H-5), 6.57(1 H, d, J 2, benzodioxan H-3), 6.63 (1 H, d, J 8, benzodioxan H-6), 7.04 (1 H, s, thiazole H-1), 7.14 (2 H, d, J 6, pyridyl H-3), 8.62 (1 H, s, pyridone CH), 8.65 (2 H, d, J 6, pyridyl H-2)

EXAMPLE 18

5-(4-Methoxyphenyl)-1-methyl-3-(4-methylthiazol-2-yl)-6-(prdrazin-2yl)-1H-pyridin-2-one Step 1: N,N-Carbonylimidazole (14.86 g) was added to a slurry of pyrazine-2-carboxylic acid in dry dimethylformamide (100 cm³). After stirring for one hour 4-methoxyphenylacetic acid t-butyl ester (10.8 g) was added. The reaction mixture was cooled to −30° C. then sodium hydride (4.62 g) was added. The reaction mixture was stirred at −30° C. for 1 h then allowed to warm to room temperature overnight. The reaction miLture was poured into water and acidified to pH 8 with acetic acid. The solution was extracted with ether (3×250 cm³). The ether extracts were combined, washed with brine, dried over magnesium sulphate filtered and evaporated under reduced pressure to give a solid. The solid was purified by chromatography using ethyl acetate/hexane (1:1) as eluant. The appropriate fractions were combined and evaporated under reduced pressure to give 2-(4-methoxyphenyl)-3-oxo-3-pyrazine-2-yl propionic acid t-butyl ester as a solid (9.8 g 61%) $\delta_H$ (250 MHz; CDCl₃) 1.39 (9 H, s, C(CH₃)3), 3.70 (3 H, s, OCH₃), 5.87(1 H, s, ᵗBuO₂CCH), 6.90 (2H, d, J 9 Hz, methoxyphenyl H-2) 7.32 (2H, d, J 9 Hz, methoxyphenyl H-3) 8.66 (1H, dd pyrazine H—) 8.74 (1H, d pyrazine H—) 9.25 (1H, d pyrazine H—)

Step 2: A mixture of 2-(4-methoxyphenyl)-3-oxo-3-pyrazine-2-yl)propionic acid t-butyl ester (9.7 g) and trifluoroacetic acid (30 cm³) were stirred at room temperature for 18 h. The reaction mixture was poured onto ice, basified with conc. ammmonia and extracted with ethyl acetate (3×250 ml). The ethyl acetate extracts were combined washed with brine dried over magnesium sulphate, filtered and evaporated under reduced pressure to give a solid. The solid was purified by chromatography using ethyl acetate as eluant. The appropriate fractions were combined and evaporated under reduced pressure to give 2-(4-methoxyphenyl)-1-(pyrazin-2-yl)ethanone as a solid (5.1 g 75%) $\delta_H$ (250MHz CDCl₃) 3.78 (3H, s, OCH₃), 4.44 (2H, s, C(O) CH₂Ar), 6.84 (2H, d, J 9, methoxyphenyl H-2), 7.24 (2H, d, J 9, methoxyphenyl H-3)) 8.66 (1H, dd pyrazine H—) 8.74 (1H, d pyrazine H—) 9.23 (1H, d pyrazine H—)

Step 3: A solution of 2-(4-methoxyphenyl)-1-(pyrazine-2-yl)ethanone (1.0 g) and dimethylformamide-dimethylacetal (10 cm³) were stirred at room temperature for 18 h. The excess rea,ent was evaporated under reduced pressure to give an oil. The oil was dissolved in tetrahydrofuran (60 cm$^3$). N-methyl 2-(4-methylthiazol-2-yl)acetamide (0.74 g) and methanol (0.36 cm$^3$) were added followed by sodium hydride (0.42 g). The reaction mixture was stirred at room temperature under nitrogen for 18 h then poured into water (500 cm$^3$) and extracted with diethyl ether (3×50 cm$^3$). The ether extracts were combined, washed with brine dried over magnesium sulphate, filtered and evaporated under reduced pressure to give an oil. The oil was purified by chromatography using dichloromethane (500 cm$^3$), dichloromethane/methanol (99:1, 500 cm$^3$) dichloromethane/methanol (98:2) as eluant. The appropriate fractions were combined and evaporated under reduced pressure to give a foam,which on tritiation with ether gave a solid. The solid was recrystallised from ethyl acetate to give 5-(4-methoxyphenyl)-1-methyl-3-(4-methylthiazol-2-yl)-6-(pyrazin-2-yl)-1H-pyridin-2-one (0. 15 g 8%) as a greenish-yellow solid m.p. 168–170° C. (Found: C, 64.48; H, 4.45; N, 14.22. $C_{21}H_{18}N_4O_2S$ requires C,64.60; H, 4.65; N, 14.35%); $\delta_H$ (360MHz; CDCl$_3$) 2.52 (3H, s, ArCH$_3$) 3.53 (3H, s, NMe), 3.74 (3H, s, OCH$_3$) 6.70(2H, d, J 9, methoxyphenyl H-2), 6.92(2H, d, J 9, methoxyphenyl H-2), 7.05 (1H, s, thiazolyl H-4) 8.25 (1H, d, J pyrazine H—), 8.52 (1H, d, J pyrazine H—) 8.72 (2H d J pyrazine H— and 1H, s, pyridone H-4); m/z (ESP+) 391 (MH$^+$).

EXAMPLE 19

5-(4-Methoxyohenyl)-6-(4-Dvridyl)-3-phenyl-1-methyl-1H-pyridin-2-one

Step 1: A solution of 2-(4-methoxyphenyl)-1-(pyridin-4-yl) ethanone (17.5 g), prepared as in Example 1 step 2, in chloroform (200 cm$^3$) was saturated with methylamine gas at 0° C. The solution was stirred under nitrogen at 0° C. whilst titanium tetrachloride in dichloromethane (1M; 40 cm$^3$) was added via syringe. After stirring the brown suspension overnight at room temperature, anhydrous sodium sulphate (5 g) was added and the yellow suspension was filtered through celite, washing with dichloromethane. Evaporation of the filtrate gave [(2-(4-methoxyphenyl)-1-pyridin-4-yl)ethylidene]methylamine (16.7 g; 90%) as an orange oil; $\delta_H$ (250 MHz; CDCl$_3$) 3.48 (3 H, broad s, NCH$_3$), 3.77 (3 H, s, OCH$_3$), 4.04 (2 H, broad s, ArCH$_2$), 6.76–6.85 (2 H, m, methoxyphenyl H-2), 6.96–7.05 (2 H. m, methoxyphenyl H-3), 7.26 and 7.58 (2 H, 2 x d, J 6, pyridyl H-3) and 8.09 (2 H, m, pyridyl H-2).

Step 2: A solution of 2-benzyloxyacetyl chloride (11.7 g) in dry THF (50 cm$^3$) was added via caninula to a stirred solution of [(2-(4-methoxyphenyl)-1-pyridin-4-yl) ethylidene]-methylamine (16.7 g) in dry THF (150 cm$^3$) at −78° C. under nitrogen. After complete addition the purple solution was warmed to 0° C. and stirred for 90 minutes. The brown suspension was poured into ice/aqueous sodium hydogencarbonate (500 cm$^3$) and extracted with ethyl acetate (2×250 cm$^3$). The extracts were washed with brine (100 cm$^3$), dried (sodium sulphate), filtered and concentrated to give a black tar. Flash column chromatogaphy on silica, eluting 5 Æ 10% methanol-dichloromethane, gave 2-benzyloxy-N-[(2-(4-methoxyphenyl)-1-pyridin-4-yl) vinyl]-N-methylacetamide (17.1 g; 64%) as a brown gum; $\delta_H$ (250 MHz; CDCl$_3$) 3.16 and 3.24 (3 H, 2×s, NCH$_3$), 3.68 and 3.73 [3 H, 2×s, OCH$_2$C(O)N], 3.85 (3 H, s, OCH$_3$), 4.36–4.50 (2 H, m, OCH$_2$Ph), 6.88–7.02 (3 H, m, C=CHAr and methoxyphenyl H-2), 7.10–7.40 (9 H. m, methoxyphenyl H-3, pyridyl H-3 and Ph), 8.44 and 8.62 (2 H, 2×d, J 6, pyridyl H-2); m/z (ESP+) 389 (MH$^+$; 100%).

Step 3: A solution of 2-benzyloxy-N-[(2-(4-methoxyphenyl)-1-pyridin-4-yl)vinyl]-N-methylacetamide (7.37 g) in the minimum volume of dichloromethane (10 cm$^3$) was added slowly at room temperature to stirred phosphorous oxychloride (12 cm$^3$). The brown solution was stirred at room temperature for 1 hour, then cooled to 0° C. before dropwise addition of dimethylformamide (3 cm$^3$). The mixture was stirred at room temperature for 1 hour, then at 75° C. for 90 minutes. The mixture was cooled to 0° C. and further dimethylformamide (1.5 cm$^3$) was added dropwise. The mixture was heated at 75° C. for 3 hours then cooled and poured onto ice (300 cm$^3$). Aqueous sodium hydroxide (2M; 150 cm$^3$) was added with vigorous stirring, followed by additional base to adjust the solution to pH 9–10. The mixture was extractd with dichloromethane (3×100 cm$^3$). The extracts were washed with water (100 cm$^3$), brine (100 cm$^3$), dried (sodium sulphate), filtered and concentrated. Flash column chromatogaphy on silica, eluting 4% methanol-dichloromethane, gave 3-(benzyloxy)-5-(4-methoxyphenyl)-6-(4-pyridyl)-1-methyl-1H-pyridin-2-one (2.12 g; 28%) as a brown foam. A sample was recrystallised m.p. 127–130° C. (EtOAc). $\delta_H$ (360 MHz; CDCl$_3$) 3.36 (3 H, s, NCH$_3$), 3.72 (3 H, s, OCH$_3$), 5.18 (2 H. s, OCH$_2$Ph), 6.65 (2 H, d, J 9, methoxyphenyl H-2), 6.76 (1 H, s, pyridone H-4), 6.78 (2 H, d, J 9, methoxyphenyl H-3), 7.04 (2 H, d, J 6, pyridyl H-3), 7.30–7.47 (5 H, m, Ph) and 8.56 (2 H, d, J 6, pyridyl H-2); m/z (ESP+) 399 (MH$^+$; 100%).

Step 5: 10% Palladium on carbon (0.5 g) was added at room temperature to a stirred solution of 3-(benzyloxy)-5-(4-methoxyphenyl)-6-(4-pyridyl)-1-methyl-1H-pyridin-2-one (1.07 g), ammonium formate (1.26 g) and glacial acetic acid (10 cm$^3$) in methanol (20 cm$^3$). After 3.5 hours the mixture was filtered and the filter-cake was washed with hydrochloric acid (1M; 150 cm$^3$). The filtrate was neutralised with saturated aqueous sodium hydrogencarbonate and extracted with dichloromethane (2×100 cm$^3$). The extracts were dried (sodium sulphate), filtered and concentrated to give 3-(4-methoxyphenyl)-6-(4-pyridyl)-3-hydroxy-1-methyl-1H-pyridin-2-one (0.62 g; 75%) as a pale pink solid. A sample was recrystallised m.p. 224–226° C. (EtOAc). Found: C, 68.8; H, 5.4; N, 8.6. $C_{18}H_{16}N_2O_3.0.1(EtOAc).0.25(H_2O)$ requires C, 68.7; H, 5.4; N, 8.7%. $\delta_H$ (360 MHz; CDCl$_3$) 3.40 (3 H, s, NCH$_3$), 3.73 (3 H, s, OCH$_3$), 6.67 (2 H, d, J 9, methoxyphenyl H-2), 6.86 (2 H, d, J 9, methoxyphenyl H-3), 6.90 (1 H, broad s, OH), 6.93 (1 H, s, pyridone H-4), 7.06 (2 H, d, J 6, pyridyl H-3) and 8.59 (2 H, d, J 6, pyridyl H-2); m/z (ESP+) 309 (MH$^+$; 100%).

Step 6: Trifluoromethanesulfonic anhydride (0.60 cm$^3$) was added dropwise at −78° C. to a stirred suspension of 3-(4-methoxyphenyl)-6-(4-pyridyl)-3-hydroxy-1-methyl-1H-pyridin-2-one (0.60 g) and pyridine (0.40 cm$^3$) in dry dichloromethane (30 cm$^3$). The brown suspension was briefly warmed to dissolve all material and then stirred at −78° C. for 1 hour. The mixture was warmed to room temperature, poured into saturated aqueous sodium hydrogencarbonate (50 cm$^3$) and extracted with dichloromethane (2×30 cm$^3$). The extracts were washed with water (50 cm$^3$), brine (30 cm$^3$), dried (sodium sulphate), filtered and evaporated to give a brown oil. Trituration with diethyl ether gave 3-trifluoromethanesulfonyl-5-(4-methoxyphenyl)-6-(4-pyridyl)-1-methyl-1-pyridin-2-one (0.78 g; 90%) as a brown solid. $\delta_H$ (360 MHz; CDCl$_3$) 3.39 (3 H, s, NCH$_3$), 3.74 (3 H, s, OCH$_3$), 6.70 (2 H, d, J 9, methoxyphenyl H-2), 6.84 (2 H, d, J 9, methoxyphenyl H-3), 7.09 (2 H, d, J 7, pyridyl H-3), 7.46 (1 H, s, pyridone H-4), and 8.64 (2 H, d, J 7, pyridyl H-2); m/z (ESP+) 441 (MH$^+$; 100%).

Step 7: A mixture of 3-trifluoromethanesulfonyl-5-(4-methoxyphenyl)-6-(4-pyridyl)-1-methyl-1H-pyridin-2-one (0.055 g), benzeneboronic acid (0.25 g) and aqueous sodium carbonate (2M; 2 cm$^3$) in dimethoxyethane (5 cm$^3$) was degassed and purged with nitrogen at room temperature. Tetrakis(triphenylphosphine)palladium (0) (0.1 g) was added and the mixture was refluxed under nitrogen for 2 hours. The mixture was diluted with water (10 cm$^3$) and extracted with ethyl acetate (3×10 cm$^3$). The extracts were dried (sodium sulphate), filtered and concentrated. Preparative thin layer chromatography, eluting with 95:5 dichloromethane-methanol, gave 5-(4-methoxyphenyl)-6-(4-pyridyl)-3-phenyl-1-methyl-1H-pyridin-2-one (0.028 g; 61%) as a pale pink foam. Recrystallised to give a beige powder m.p. 183–185° C. (EtOAc-hexane). $\delta_H$ (360 MHz; CDCl$_3$) 3.39 (3 H, s, NCH$_3$), 3.73 (3 H, s, OCH$_3$), 6.69 (2 H, d, J 9, methoxyphenyl H-2), 6.90 (2 H, d, J 9, methoxyphenyl H-3), 7.13 (2 H, d, J 6, pyridyl H-3), 7.35–7.44 (3 H, m, 3 of Ph), 7.59 (1 H, s, pyridone H-4), 7.77 (2 H, d, J 8, 2 of Ph) and 8.60 (2 H, d, J 6, pyridyl H-2); m/z (ESP+) 369 (MH$^+$; 100%).

EXAMPLE 20

5-(4-Methoxyohenyl)-3-(3-methylisothiazol-5-yl)-6-(4-pyridyl)-1-methyl-1H-pyridin-2-one A solution of n-butyllithium in hexanes (1.6 M; 7 cm$^3$) was added dropwise at −78° C. to a stirred solution of 3-methylisothiazole (1.0 g) in dry tetrahydrofuran (30 cm$^3$) under nitrogen. After stirring the orange suspension for 40 minutes, trimethyl borate (1.35 cm$^3$) was added and the colourless solution was warmed to room temperature over 2 hours. Water (2.2 cm$^3$) was added and the solution was stirred overnight, then diluted with diethyl ether (50 cm$^3$) and the off-white precipitate collected to give hydrated 3-methylisothiazol-5-ylboronic acid (2.1 g). A mixture of the boronic acid (0.35 g), 3-trifluoromethanesulfonyl-5-(4-methoxyphenyl)-6-(4-pyridyl)-1-methyl-1H-pyridin-2-one (Example 13 Step 6) (0.35 g), aqueous sodium carbonate (2M; 1 cm$^3$) and tetrahis(triphenylphosphine) palladium (0) (0.1 g) in dimethoxyethane (20 cm$^3$) was degassed and purged with nitrogen at room temperature, then refluxed under nitrogen for 1.5 hours. The mixture was cooled, diluted with water (40 cm$^3$) and extracted with ethyl acetate (3×20 cm$^3$). The extracts were dried (magnesium sulphate), filtered and concentrated. The resulting solid was redissolved in ethyl acetate (20 cm$^3$) and extracted with dilute hydrochloric acid (1M; 2×30 cm$^3$). The acidic extracts were basified to pH 10 with aqueous sodium hydroxide (4M) and the resultant white precipitate was collected. Preparative thin layer chromatography, eluting 95:5 dichloromethane-methanol, gave 5-(4-methoxyphenyl)-3-(3-methylisothiazol-5-yl)-6-(4-pyridyl)-1-methyl-1H-pyridin-2-one (0.028 g; 12 %) as a bright yellow solid m.p. 195–198° C. Found: C, 67.5; H, 4.7. $C_{22}H_{19}N_3O_2S$. 0.1 (H$_2$O) requires C, 67.5; H, 4.95%. $\delta_H$ (360 MHz; CDCl$_3$) 2.55 (3 H, s, ArCH$_3$), 3.49 (3 H, s, NCH$_3$), 3.76 (3 H, s, OCH$_3$), 6.74 (2 H, J 9, methoxyphenyl H-2), 6.90 (2 H, d, J 9, methoxyphenyl H-3), 7.20 (2 H, d, J 6, pyridyl H-3), 7.42 (1 H, s, pyridone H-4), 8.01 (1 H, s, isothiazole H-4) and 8.66 (2 H, d, J6, pyridyl H-2); m/z (ESP+) 390 (MH$^+$; 100%).

EXAMPLE 21

1-Methyl-3-(4-methylthiazol-2-yl)-5-(N-methyl-N-benzylamino)-6-(4-pyridyl)-1H-pyridin-2-one.

Step 1: To a solution of N-benzyl-N-methylamine (3.7 cm$^3$) in dry dichloromethane (40 cm$^3$), cooled to 0° C. was added with stirring, 4-bromoacetylpyridine hydrobromide (4.0 g). The reaction was allowed to warm to room temperature, then stirred for a further 18 hr. The solvent was stripped at reduced pressure, and the residue partitioned between ethyl acetate and dilute aqueous Na$_2$CO$_3$. The organic phase was separated, dried (Na$_2$SO$_4$), evaporated, and the residue subjected to chromatography on silica gel, eluent 5% methanol in dichloromethane, to afford 4-(N-benzyl-N-methylaminoacetyl)pyridine, 1.49 g, 43%, as a yellow gum.

Step 2: To a solution of 4-(N-benzyl-N-methylaminoacetyl) pyridine (1.49 g, 6.2 mmol) in dry dimethylformamide (10 cm$^3$), was added dimethylformamide dimethylacetal (10 cm$^3$). The reaction was stirred at room temperature for 18 hr. The reaction mixture was then diluted with toluene (25 cm$^3$), and the solvents stripped at reduced pressure. The residue was dissolved in dry dimethylformamide (20 cm$^3$), and 4-methylthiazole-2-(N-methyl)acetamide (1.05 g), and dry methanol (0.553 cm$^3$) added. To this stirred mixture, cooled under an argon atmosphere to 0° C. was added with stirring sodium hydride (0.545 g of a 60% dispersion in oil). The reaction was allowed to warm to room temperature, then stirred for a further 72 hr. The reaction mixture was partitioned between ethyl acetate and water. The organic phase was separated, dried (Na$_2$SO$_4$), evaporated, and the residue subjected to chromatography on silica gel, eluent 2% methanol in dichloromethane, to afford the title compound. Treatment with a solution of hydrogen chloride in methanol afforded the bis-hydrochloride salt, crystallised from hot methanol-dichloromethane-ethyl acetate mixtures, as an orange solid. Found C, 54.65; H, 5.36; N, 11.05% $C_{23}H_{22}NO_1S_1$.(HCl)$_2$. (H$_2$O)$_{1.5}$ requires C, 54.98; H, 5.42; N, 11.15%). m/e (ES$^+$) 403 MH$^+$.

EXAMPLE 22

1-Methyl-3, 5-diphenyl-6-(4-pyridynl)-1H-ivrazin-2-one

Step 1: To a cooled (0° C.) solution of 3,5-diphenyl-6-chloro-1H-pyrazin-2-one (1.2 g; prepared by the method of Cheeseman et al, J. Chem. Soc. Chem. Comm. 1971, (18), 2977–2979) in 4:1 ethylene glycol dimethylether: dimethylformamide (25 cm$^3$)was added sodium hydride (0.28 g). The reaction was stirred for 5 minutes at 0° C. under nitrogen whereupon lithium bromide (1.17 g) was added. After a further 5 minutes stirring at room temperature, under nitrogen, methyl iodide (4.78 g) was added. The mixture was stirred at room temperature overnight under nitrogen. The reaction was diluted with water and extracted with ethyl acetate. The organic phase was separated, dried over sodium sulphate and evaporated in vacuo. The residue was subjected to chromatography on silica gel using ethyl acetate as eluant to afford 1-methyl-3,5-diphenyl-6-chloro-1H-pyrazin-2-one as a yellow solid (1.2 g; 60%). Found C, 68.98; H, 4.31; N, 8.98% $C_{17}H_{13}N_2OCl$ requires C, 68.81; H, 4.42; N, 9.44%.m/e (ES$^+$) 297/299 (M+H)$^+$.

Step 2: To a solution of 1-methyl-3,5-diphenyl-6-chloro-1H-pyrazin-2-one (0.5 g) in 3:1 ethylene glycol dimethylether : water (30 cm$^3$), under nitrogen, was added sequentially 4-pyridyl boronic acid lithium salt (0.42 g), sodium carbonate (0.72 g) and tetrakis-triphenylphosphine palladium (0.07 g). The reaction was heated at reflux, under nitrogen, overnight. The solvents were evaporated and the residue partitioned between water and 5% methanol/dichloromethane. The organic phase was separated, dried over magnesium sulphate and evaporated in vacuo. The residue was subjected to silica gel chromatography using 2% methanol/dichloromethane as eluant. The product was treated with hydrogen chloride in methanol and recrystallised from ethyl acetate/diethyl ether to afford 1-methyl-3,5-diphenyl-6-(4-pyridyl)-1H-pyrazin-2-one hydrochloride(0.2 g ; 32%) as yellow crystals. Found C, 70.50; H, 4.90; N, 11.20% $C_{22}H_{17}N_3O.HCl$ requires C, 70.30; H, 4.83; N, 11.18%.m/e (ES+) 340 (M+H)+.

EXAMPLE 23

5-(4-Methoxylhenyl)-1-methyl-3-(4-methylthiazol-2-yl)-6-(4-morpholino)-1H-pyridin-2-one Step 1: Methyl 4-methoxyphenylacetate (3.3 g) was dissolved in N,N-5 dimethylformamide (3 cm³) treated with N,N-dimethylformamide dimethyl acetal (6 cm³) and heated at 100° C. for 18 h. The reaction was then cooled and evaporated under high vacuum to afford crude methyl-3-dimethylamino-2-(4-methoxyphenyl)propenoate (3.6 g) which was used without further purification. $\delta_H$ (250 MHz; CDCl₃); 2.68 (6H, s), 3.62 (3H, s), 3.8 (3H, s), 6.82 (2H, d, J8.7 Hz), 71 (2H, d, J8.7 Hz) and 7.54 (1H, s).

Step 2: Methyl-3-dimethylamino-2-(4-methoxyphenyl) propenoate (1.6 g), N-methyl-2-(4-methylthiazol-2-yl) acetamide (1 g) and methanol (0.28 cm³) were dissolved in N,N-dimethylformamide (30 cm³) and cooled to 0° C. under N₂. Sodium hydride (60% suspension in oil, 0.28 g) was added and the mixture heated at 80° C. for 18 h. The mixture was cooled, partitioned between ethyl acetate (200 cm³) and water (200 cm³). The aqueous layer was acidified with 2N HCl and extracted with ethyl acetate (3×100 cm³) which was dried (MgSO₄) ) and evaporated. The crude solid was recrystaolised from e thyl acetate/ether to yield pure 6-hydroxy-5-(4-methoxyphenyl)-1-methyl-3-(4-methylthiazol-2-yl)-1H-pyridin-2-one (0.3 g). $\delta_H$ (250 MHz; CDCl₃); 2.37 (3H, s), 3.48 (3H, s), 3.83 (3 H, s), 6.37 (1H, s), 6.92 (2H, d, J 8. 7 Hz), 7.33 (1H, s) and 7.53 (2H, d, J 8.7 Hz); m/z (ESP+) 329 (MH+).

Step 3: 6-Hydroxy-5-(4-methoxyphenyl)-1-methyl-3-(4-methylthiazol-2-yl)-1H-pyridin-2-one (0.13 g) was dissolved in freshly distilled POCl₃ (5 cm³) under N₂ and heated to reflux for 1.5 h. The excess reagent was then removed by evaporation and the residue partitioned between ethyl acetate (100 cm³) and saturated sodium bicarbonate solution (50 cm³). The aqueous layer was washed with ethyl acetate (2×100 cm³) and the combined organic phase dried (MgSO₄) and evaporated. Purification on silica gel eluting with ethyl acetate-hexane mixtures afforded 6-chloro-5-(4-methoxyphenyl)-1-methyl-3-(4-methylthiazol-2-yl)-1H-pyridin-2-one as a yellow powder. $\delta_H$ (250 MHz; CDCl₃); 2.49 (3H, s), 3.86 (3H, s), 3.93 (3H, s), 6.96 (2H, d, J8.7 Hz), 7.01 (1H, s) 7.33 (2H, d, J8.7 Hz) and 8.60 (1H, s).

Step 4: 6-Chloro-5-(4-Methoxyphenyl)-1-methyl-3-(4-methylthiazol-2-yl)-1H-pyridin-2-one (0.3 g) was dissolved in DMSO (10 cm³), treated with morpholine (2 cm³) and heated to 100° C. for 18 h. The reaction was then poured into diethyl ether:ethyl acetate (1:1, 100 cm³) and washed with brine (30 cm³). The aqueous phase was extracted with diethyl ether:ethyl acetate (1:1, 2×100 cm³) and the combined organic phase dried (MgSO₄) and evaporated to dryness. The residue was purified on silica gel eluting with ethyl acetate mixtures to give 0.13 g of 5-(4-methoxyphenyl)-1-methyl-3-(4-methylthiazol-2-yl)-6-(4-morpholino)-1H-pyridin-2-one as a pale yellow powder. $\delta_H$ (250 MHz; CDCl3); 2.48 (3H, s), 2.8 (4H, t, J 4.2 Hz), 3.68 (4H, t, J 4.2 Hz) 3.79 (3H, s), 3.86 (3H, s), 6.95 (2H, d, J 8.6 Hz), 7.17 (2H, d, J 8.6 Hz) and 8.56 (1H, s); m/z (ESP+) 398 (MH+).

EXAMPLE 24

6-Dimethylamino-5-(4-Methoxyphenyl)-1-methyl-3-(4-methylthiazol-2-yl)-1H-pyridin-2-one This compound was prepared as for Example 23 replacing morpholine with dimethylamine in Step 4. $\delta_H$ (250 MHz; CDCl3); 2.47 (3H, s), 2.59 (6H, s), 3.70 (3H, s), 3.85 (3H, s), 6.91 (1H, s), 6.94 (2H, d, J 8.7 Hz), 7.17 (2H, d, J 8.7 Hz) and 8.50 (1H, s); m/z (ESP+) 356 (MH+).

EXAMPLE 25

1-Methyl-3-(4-methylthiazol-2-yl)-6-(4-morpholino)-1H-5-(4-pyridinyl)pyridin-2-one Step 1: Methyl-4-pyridinylacetate (6.3 g) was dissolved in N,N-dimethylformamide (30 cm³) treated with N,N-dimethylformamide dimethyl acetal (15 cm³) and heated at 80° C. for 2 h. The reaction was then cooled and evaporated under high vacuum to afford crude methyl-3-dimethylamino-2-(pyridin-4-yl)propenoate (7.3 g) which was used without further purification.

Step 2: 6-Hydroxy-1-methyl-3-(4-methylthiazol-2-yl)-1H-5-(4-pyridinyl)pyridin-2-one was prepared as in Example 17 Step 2 replacing methyl-3-dimethylamino-2-(4-methoxyphenyl)propenoate with methyl-3-dimethylamino-2-(pyridin-4-yl)propenoate. $\delta_H$ (250 MHz; d6-DMSO); 2.76 (3H, s), 3.54 (3H, s), 7.40 (1H, s), 8.85 (2H, d, J 6.9 Hz), 8.93 (2H, d, J 6.9 Hz) and 9.51 (1H, s); m/z (ESP+) 300 (MH+).

Step 3: 6-Chloro-1-methyl-3-(4-methylthiazol-2-yl)-1H-5-(4-pyridinyl)pyridin-2-one was prepared as in Example 17 Step 3 replacing 6-hydroxy-5-(4-methoxyphenyl)-1-methyl-3-(4-methylthiazol-2-yl)-1H-pyridin-2-one with 6-hydroxy-1 -methyl-3-(4-methylthiazol-2-yl)-1H-5-(4-pyridinyl)pyridin-2-one. $\delta_H$ (250 MHz; d6-DMSO); 2.4 (3H, s), 3.94 (3H, s), 7.37 (1H, s), 7.64 (2H, d, J6.1 Hz), 8.31 (1H, s) and 8.72 (2H, d, J6.9 Hz); m/z (ESP+) 318 and 320 (MH+).

Step 4: 1-Methyl-3-(4-methylthiazol-2-yl)-6-(4-morpholino)-1H-5-(4-pyridinyl)pyridin-2-one compound was prepared as for Example 17 Step 4 replacing 6-chloro-5-(4-methoxyphenyl)-1-methyl-3-(4-methylthiazol-2-yl)-1H-pyridin-2-one with 6-chloro-1-methyl-3-(4-methylthiazol-2-yl)-1H-5-(4-pyridinyl)pyridin-2-one. $\delta_H$ (250 MHz; CDCl₃); 2.48 (3H, s), 2.86 (4H, m), 3.72 (4H, m), 3.79 (3H, s), 6.96 (1H, s), 7.24 (2H, m), 8.41 (1H, s) and 8.72 (2H, m); m/z (ESP+) 369 (MH+).

EXAMPLE 26

1-Methyl-3-(4-methylthiazol-2-yl)-6-(1-Pyrrolidino)-1H-5-(4-pyridinyl)pyridin-2-one The titled compound was prepared as for Example 25 replacing morpholine with pyrrolidine in Step 4. $\delta_H$ (250 MHz; CDCl3); 1.83–1.88 (4H, m), 2.48 (3H, d, J 0.5Hz), 3.07 (4H, t, J 6.6Hz), 3.66 (3H, s), 6.93 (1H d, J 0.7Hz), 7.22 (2H, dd, J 1.6 and 3.7Hz), 8.44 (1H, s) and 8.68 (2H, J 1.6 and 3.7Hz); m/z (ESP+) 353 (MH+).

The following Examples have also been prepared in an analogous manner to the preceding Examples.

| Ex | Z | Y | X | R |
|----|---|---|---|---|
| 27 | pyridin-4-yl | 4-methoxyphenyl | 5-cyclopropyl-1,2,4-oxadiazol-3-yl | Me |
| 28 | pyridin-4-yl | 4-methoxyphenyl | 3-methyl-1,2,4-thiadiazol-5-yl | Me |
| 29 | pyridin-4-yl | 4-methoxyphenyl | 5-isopropyl-1,2,4-oxadiazol-3-yl | Me |
| 30 | pyridin-4-yl | 4-methoxyphenyl | 3-cyclopropyl-1,2,4-thiadiazol-5-yl | Me |
| 31 | 5-methylfuran-2-yl | 4-methoxyphenyl | 5-methyl-1,2,4-oxadiazol-3-yl | Me |
| 32 | thiophen-2-yl | 4-methoxyphenyl | thiazol-2-yl | Me |
| 33 | thiophen-3-yl | 4-methoxyphenyl | 5-cyclopropyl-1,2,4-oxadiazol-3-yl | Me |

-continued

| Ex | Z | Y | X | R |
|---|---|---|---|---|
| 34 | 5-methylfuran-2-yl | 4-MeO-phenyl | 5-cyclopropyl-1,2,4-oxadiazol-3-yl | Me |
| 35 | pyridin-4-yl | 4-MeO-phenyl | 4-ethylthiazol-2-yl | Me |
| 36 | pyridin-4-yl | pyridin-4-yl | 4-methylthiazol-2-yl | Me |
| 37 | pyridin-4-yl | H | 4-methylthiazol-2-yl | Me |
| 38 | pyridin-3-yl | 4-MeO-phenyl | 4-methylthiazol-2-yl | Me |
| 39 | pyridin-4-yl | 4-MeO-phenyl | 4,5-dihydrothiazol-2-yl | Me |
| 40 | pyridin-4-yl | 4-F-phenyl | 4-methylthiazol-2-yl | Me |

-continued

| Ex | Z | Y | X | R |
|---|---|---|---|---|
| 41 | 4-pyridyl | 4-(hydroxymethyl)phenyl | 4-methylthiazol-2-yl | Me |
| 42 | 2-thienyl | 4-pyridyl | 4-methylthiazol-2-yl | Me |
| 43 | 4-pyridyl | phenyl | 4-methylthiazol-2-yl | Me |
| 44 | 4-pyridyl | 4-methoxyphenyl | 4-methylthiazol-2-yl | Et |
| 45 | 4-pyridyl | 4-methoxyphenyl | thiazol-4-yl | Me |
| 46 | 4-pyridyl | 4-(dimethylamino)phenyl | 4-methylthiazol-2-yl | Me |
| 47 | 4-methoxyphenyl | 4-pyridyl | 4-methylthiazol-2-yl | Me |

-continued

| Ex | Z | Y | X | R |
|---|---|---|---|---|
| 48 | 4-pyridyl | benzo[1,3]dioxol-5-yl | 4-methylthiazol-2-yl | Me |
| 49 | 4-pyridyl | 3,4-dimethoxyphenyl | 4-methylthiazol-2-yl | Me |
| 50 | 1H-imidazol-4-yl | 4-methoxyphenyl | 4-methylthiazol-2-yl | Me |
| 51 | thiophen-3-yl | 4-methoxyphenyl | 4-methylthiazol-2-yl | Me |
| 52 | thiophen-2-yl | 4-methoxyphenyl | 4-methylthiazol-2-yl | Me |
| 53 | 4-pyridyl | 4-methoxyphenyl | 4-methylthiazol-2-yl | HOCH$_2$CH$_2$— |
| 54 | 4-pyridyl | 4-fluorophenyl | thiazol-4-yl | Me |

-continued

| Ex | Z | Y | X | R |
|---|---|---|---|---|
| 55 | 4-pyridyl | 4-fluorophenyl | 4-methylthiazol-2-yl | Me |
| 56 | 4-pyridyl | pyrimidin-4-yl | 4-methylthiazol-2-yl | Me |
| 57 | thiophen-2-yl | 4-(hydroxymethyl)phenyl | 4-methylthiazol-2-yl | Me |
| 58 | 4-pyridyl | 4-hydroxyphenyl | 4-methylthiazol-2-yl | Me |
| 59 | 4-pyridyl | 4-methylphenyl | 4-methylthiazol-2-yl | Me |
| 60 | 4-pyridyl | 4-isopropoxyphenyl | 4-methylthiazol-2-yl | Me |
| 61 | thiophen-2-yl | 4-methoxyphenyl | 4-methylthiazol-2-yl | HOCH$_2$CH$_2$— |

-continued

| Ex | Z | Y | X | R |
|---|---|---|---|---|
| 62 | 2-thienyl | 4-MeO-phenyl | 4-methylthiazol-2-yl | FCH$_2$CH$_2$— |
| 63 | pyridin-4-yl | 4-Cl-phenyl | 4-methylthiazol-2-yl | Me |
| 64 | pyrimidin-4-yl | 4-MeO-phenyl | 4-methylthiazol-2-yl | H |
| 65 | phenyl | 4-MeO-phenyl | 4-methylthiazol-2-yl | Me |
| 66 | pyridin-4-yl | 4-MeO-phenyl | 4-chlorothiazol-2-yl | Me |
| 67 | pyridin-4-yl | 4-Br-phenyl | 4-methylthiazol-2-yl | Me |
| 68 | pyridin-4-yl | 2,6-difluorophenyl | 4-methylthiazol-2-yl | Me |

-continued
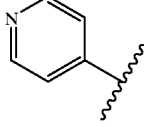
| Ex | Z | Y | X | R |
|---|---|---|---|---|
| 69 | 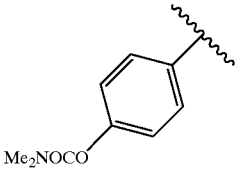 | 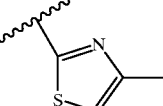 | 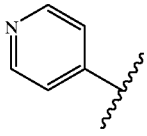 | Me |
| 70 | 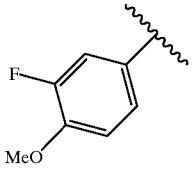 | 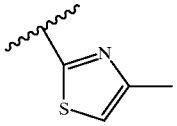 | 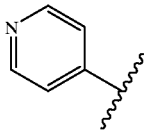 | Me |
| 71 | 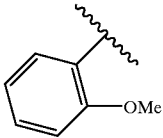 | 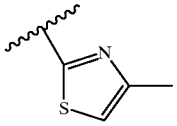 | 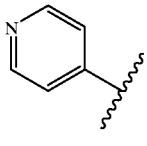 | Me |
| 72 | 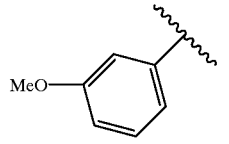 | 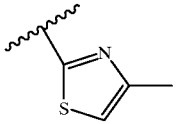 | 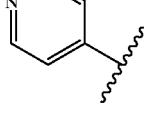 | Me |
| 73 | 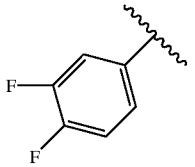 | 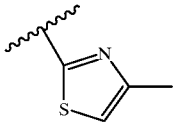 | 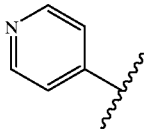 | Me |
| 74 | 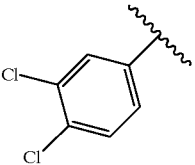 | 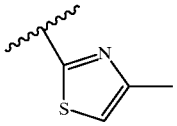 | 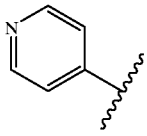 | Me |
| 75 | 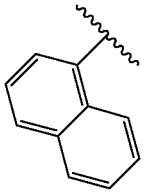 | 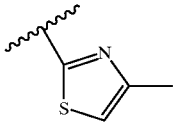 | | Me |

-continued
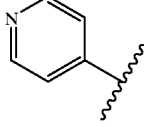
| Ex | Z | Y | X | R |
|---|---|---|---|---|
| 76 | 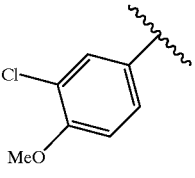 | 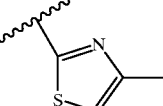 | 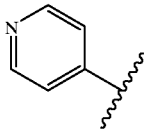 | Me |
| 77 | 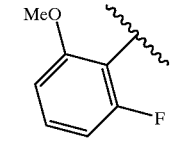 | 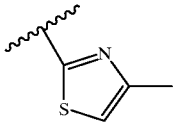 | 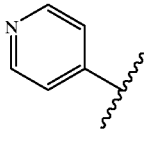 | Me |
| 78 | 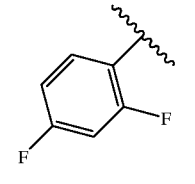 | 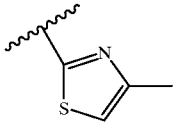 | 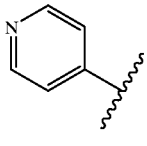 | Me |
| 79 | 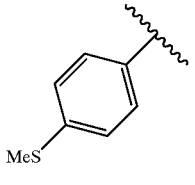 | 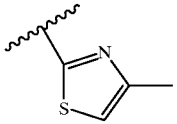 | 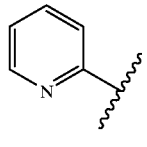 | Me |
| 80 | 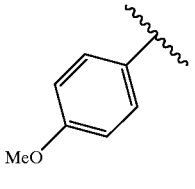 | 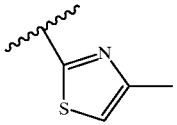 | 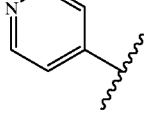 | Me |
| 81 | 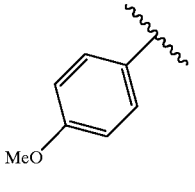 | 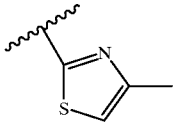 | 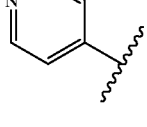 | $CH_2=CHCH_2-$ |
| 82 | 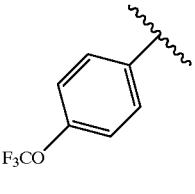 | 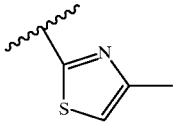 | | Me |

-continued

| Ex | Z | Y | X | R |
|---|---|---|---|---|
| 83 | 4-pyridyl | 4-methoxy-3-methylphenyl | 4-methylthiazol-2-yl | Me |
| 84 | pyridazin-4-yl | 4-methoxyphenyl | 3-methyl-1,2,4-thiadiazol-5-yl | Me |
| 85 | pyridazin-4-yl | 2,3-dihydrobenzo[1,4]dioxin-6-yl | 4-methylthiazol-2-yl | Me |
| 86 | pyridazin-4-yl | 2,3-dihydrobenzo[1,4]dioxin-6-yl | 3-methyl-1,2,4-thiadiazol-5-yl | Me |
| 87 | pyridazin-4-yl | benzo[1,3]dioxol-5-yl | 3-methyl-1,2,4-thiadiazol-5-yl | Me |
| 88 | 4-pyridyl | thiophen-3-yl | 4-methylthiazol-2-yl | Me |
| 89 | piperidin-1-yl | 4-methoxyphenyl | 4-methylthiazol-2-yl | Me |

-continued

|     |   |   |   |   |
|-----|---|---|---|---|
| Ex  | Z | Y | X | R |
| 90  | Cl | 4-pyridyl | 4-methylthiazol-2-yl | Me |
| 91  | 4-pyridyl | 4-biphenylyl | 4-methylthiazol-2-yl | Me |
| 92  | 4-pyridyl | 2-thienyl | phenyl | Me |
| 93  | phenyl | (pyridin-2-yl)methoxy | 4-methylthiazol-2-yl | Me |
| 94  | 4-pyridyl | phenyl | 3-thienyl | Me |
| 95  | 4-pyridyl | 4-methoxyphenyl | 3-aminophenyl | Me |
| 96  | 4-pyridyl | 4-(pyridin-4-yl)phenyl | 4-methylthiazol-2-yl | Me |

-continued

| Ex | Z | Y | X | R |
|---|---|---|---|---|
| 97 | pyridin-4-yl | 4-methoxyphenyl | 3-fluorophenyl | Me |
| 98 | pyridin-3-yl | 2,3-dihydro-1,4-benzodioxin-6-yl | 4-methylthiazol-2-yl | Me |
| 99 | morpholin-4-yl | 2,3-dihydro-1,4-benzodioxin-6-yl | 4-methylthiazol-2-yl | Me |
| 100 | pyrrolidin-1-yl | 2,3-dihydro-1,4-benzodioxin-6-yl | 4-methylthiazol-2-yl | Me |
| 101 | pyrrolidin-1-yl | 4-methoxyphenyl | 4-methylthiazol-2-yl | Me |
| 102 | MeNH— | 4-methoxyphenyl | 4-methylthiazol-2-yl | Me |
| 103 | pyridin-4-yl | 4-ethoxyphenyl | 4-methylthiazol-2-yl | Me |

-continued

| Ex | Z | Y | X | R |
|---|---|---|---|---|
| 104 | 4-pyridyl | 3-(trifluoromethyl)phenyl | 4-methylthiazol-2-yl | Me |
| 105 | 4-pyridyl | 4-ethylphenyl | 4-methylthiazol-2-yl | Me |
| 106 | 4-pyridyl | 4-methoxyphenyl | 2-pyridyl | Me |
| 107 | 4-pyridyl | benzo[b]thiophen-3-yl | 4-methylthiazol-2-yl | Me |
| 108 | 4-pyridyl | 2,4,6-trifluorophenyl | 4-methylthiazol-2-yl | Me |
| 109 | 4-pyridyl | 2,6-difluoro-4-methoxyphenyl | 4-methylthiazol-2-yl | Me |
| 110 | 4-pyridyl | 2,4-difluoro-6-methoxyphenyl | 4-methylthiazol-2-yl | Me |

-continued

| Ex | Z | Y | X | R |
|---|---|---|---|---|
| 111 | pyridin-4-yl | 3-fluoro-2-methylphenyl | 4-methylthiazol-2-yl | Me |
| 112 | pyridin-3-yl | benzyloxy | 4-methylthiazol-2-yl | Me |
| 113 | pyridin-4-yl | 3-fluorophenyl | 4-methylthiazol-2-yl | Me |
| 114 | pyridin-4-yl | 2-fluorophenyl | 4-methylthiazol-2-yl | Me |
| 115 | pyridin-4-yl | 3-methoxy-4-methylphenyl | 4-methylthiazol-2-yl | Me |
| 116 | pyrazin-2-yl | benzyloxy | 4-methylthiazol-2-yl | Me |
| 117 | pyridin-4-yl | 2-methylphenyl | 4-methylthiazol-2-yl | Me |

-continued
| Ex | Z | Y | X | R |
|---|---|---|---|---|
| 118 | 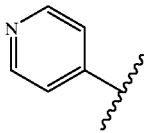 | 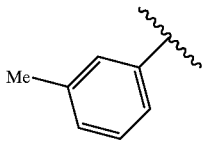 | 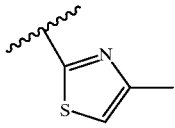 | Me |
| 119 | 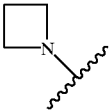 | 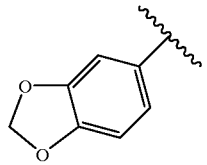 | 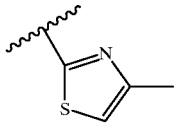 | Me |
| 120 | 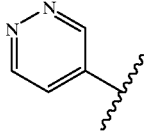 | 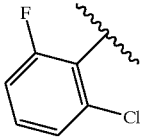 | 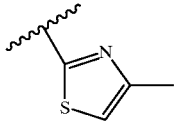 | Me |
| 121 | 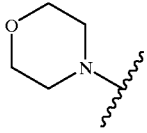 | 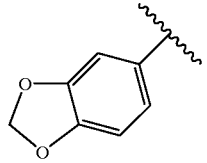 | 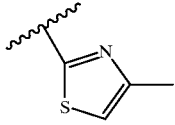 | Me |
| 122 | MeS— | 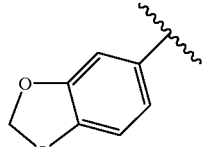 | 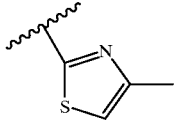 | Me |
| 123 | HOCH$_2$CH$_2$NH— | 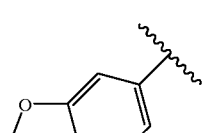 |  | Me |
| 124 | 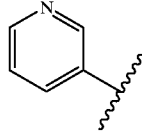 | 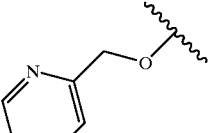 | 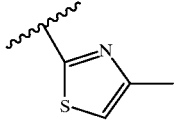 | Me |

-continued
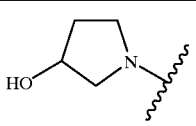
| Ex | Z | Y | X | R |
|---|---|---|---|---|
| 125 | 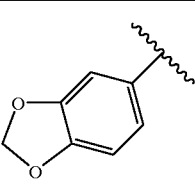 | 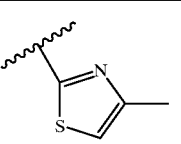 | 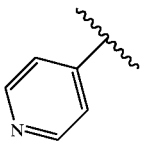 | Me |
| 126 | MeNH— | 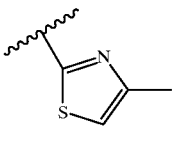 | 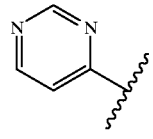 | Me |
| 127 | 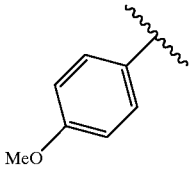 | 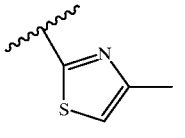 | 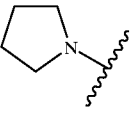 | Me |
| 128 | 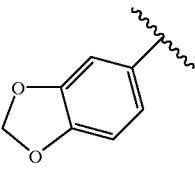 | 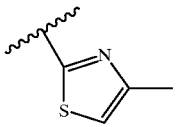 | 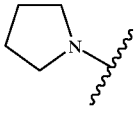 | Me |
| 129 | 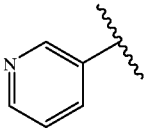 | 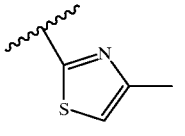 | 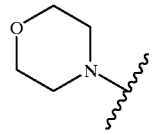 | Me |
| 130 | 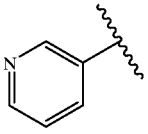 | 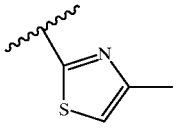 | 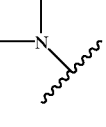 | Me |
| 131 | 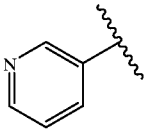 | 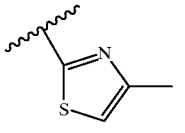 | 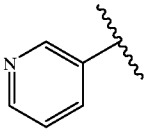 | Me |
| 132 | Me$_2$N— | 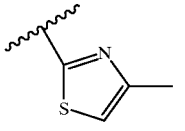 | | Me |

-continued

| Ex | Z | Y | X | R |
|---|---|---|---|---|
| 133 | Me₂N— | 4-pyridyl | 4-methylthiazol-2-yl | Me |
| 134 | piperidin-1-yl | benzo[1,3]dioxol-5-yl | 4-methylthiazol-2-yl | Me |
| 135 | furan-2-yl | benzo[1,3]dioxol-5-yl | 4-methylthiazol-2-yl | Me |
| 136 | thiomorpholin-4-yl | benzo[1,3]dioxol-5-yl | 4-methylthiazol-2-yl | Me |
| 137 | 4-pyridyl | 3-pyridyl | 4-methylthiazol-2-yl | Me |
| 138 | 1H-imidazol-4-yl | PhCH₂NH— | 4-methylthiazol-2-yl | Me |
| 139 | 4-pyridyl | 2,3-dihydrobenzo[1,4]dioxin-6-yl | thiophen-2-yl | Me |

-continued

| Ex | Z | Y | X | R |
|----|---|---|---|---|
| 140 | 4-pyridyl | 2,3-dihydro-1,4-benzodioxin-6-yl | 3-thienyl | Me |
| 141 | azetidin-1-yl | 2-thienyl | 2-pyridyl | Me |
| 142 | MeNH— | 1,3-benzodioxol-5-yl | 4-methylthiazol-2-yl | CH$_2$=CHCH$_2$— |
| 143 | 3-pyridyl | (pyridin-4-yl)methoxy | 4-methylthiazol-2-yl | Me |
| 144 | 3-pyridyl | (pyridin-3-yl)methoxy | 4-methylthiazol-2-yl | Me |
| 145 | morpholin-4-yl | 2-pyridyl | 4-methylthiazol-2-yl | Me |
| 146 | H$_2$N— | 2-pyridyl | 3-thienyl | Me |
| 147 | 3-pyridyl | 2-pyridyl | 4-methylthiazol-2-yl | Me |

-continued

| Ex | Z | Y | X | R |
|---|---|---|---|---|
| 148 | pyrrolidin-1-yl | PhCH2NH- | thiazol-2-yl (4-Me) | Me |
| 149 | cyclopropyl | 4-MeO-C6H4- | thiazol-2-yl (4-Me) | Me |
| 150 | pyridin-3-yl | 4-Me-C6H4-CH2O- | thiazol-2-yl (4-Me) | Me |
| 151 | pyridin-3-yl | 3-Me-C6H4-CH2O- | thiazol-2-yl (4-Me) | Me |
| 152 | MeNH— | benzo[1,3]dioxol-5-yl | thiazol-2-yl (4-Me) | Me |
| 153 | pyridin-3-yl | 2-Me-C6H4-CH2O- | thiazol-2-yl (4-Me) | Me |
| 154 | cyclopentyl | pyridin-2-yl | thiazol-2-yl (4-Me) | Me |

-continued

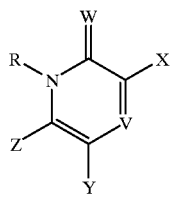

| Ex | Z | Y | X | R |
|---|---|---|---|---|
| 155 | cyclopropyl | 2-pyridyl | thiazol-2-yl | Me |
| 156 | phenyl | benzylamino (PhCH₂NH–) | thiazol-2-yl | Me |
| 157 | 4-pyridyl | benzylamino (PhCH₂NH–) | thiazol-2-yl | Me |
| 158 | cyclobutyl | 2-pyridyl | thiazol-2-yl | Me |
| 159 | 4-pyridyl | (2-pyridyl)CH₂O– | thiazol-2-yl | Me |

What is claimed is:

1. A compound of formula I or a salt thereof:

(I)

wherein:
R is hydrogen, $C_{1-6}$alkyl, $C_{2-6}$alkenyl, $C_{2-6}$alkynyl, $C_{1-6}$alkoxy, $C_{2-6}$alkenyloxy or $C_{2-6}$alkynyloxy, and when R is not hydrogen, R is optionally independently substituted by one or more halogen atoms or hydroxy, cyano or amino groups;
V is CH;
W is O;
X is a five-membered heteroaromatic group containing one, two, three or four heteroatoms independently selected from N, O and S providing that not more than one heteroatom is selected from O and S, the heteroaromatic group being unsubstituted or substituted with one or more groups independently selected from halogen, $C_{1-6}$alkyl, $C_{2-6}$alkenyl, $C_{2-6}$alkynyl, $C_{3-6}$cycloalkyl, $C_{4-6}$cycloalkenyl and $CF_3$;
Y is hydrogen, $NR^1R^2$, $C_{1-6}$alkyl, $C_{2-6}$alkenyl, $C_{2-6}$alkynyl, Ar, $O(CH_2)_nAr^1$ or $C_kH_{2k-4}Ar^2$;
$R^1$ and $R^2$ are independently selected from hydrogen, $C_{1-6}$alkyl, $C_{2-6}$alkenyl, $C_{2-6}$alkynyl, $C_{1-6}$hydroxyalkyl and $(CH_2)_mAr^3$,
Ar is thienyl, furyl or a six-membered heteroaromatic ring containing one or two nitrogen atoms which is unsubstituted or subtituted with one or more groups independently selected from halogen and $C_{1-6}$alkyl groups and which is optionally fused to a benzene ring; or napththyl or phenyl rings which rings are unsubstituted or substituted with one or more groups independently selected from halogen, cyano, amino, nitro, $C_{1-6}$alkyl, $C_{2-6}$alkenyl, $C_{2-6}$alkynyl, $CF_3$, $CF_3O$, $C_{1-6}$alkoxy, $C_{2-6}$alkenyloxy, $C_{2-6}$alkynyloxy, $C_{1-6}$alkythio, $C_{2-6}$alkenylthio, $C_{2-6}$alkynylthio, hydroxy, hydroxy$C_{1-6}$alkyl, $NR^3R^4$, $OC(O)NR^3R^4$, $C_{1-6}$alkoxyphenyl$C_{1-6}$alkoxy, cyano$C_{1-6}$alkyl, cyano$C_{2-6}$alkenyl, cyano$C_{2-6}$alkynyl, pyridil, phenyl, $C_{1-6}$alkoxycarbonyl, $C_{1-6}$alkoxycarbonyl$C_{1-6}$alkyl, $C_{1-6}$alkoxycarconyl$C_{2-6}$alkenyl, $C_{1-6}$alkoxycarbonyl$C_{2-6}$alkynyl and —$O(CH_2)_pO$— and which is optionally fused to a benzene ring;

$Ar^1$, $Ar^2$, and $Ar^3$ are independently selected from pyridyl; and phenyl which is unsubstituted or substituted with one or more groups independently selected from halogen, cyano, amino, nitro, $C_{1-6}$alkyl, $C_{2-6}$alkenyl, $C_{2-6}$alkynyl, $CF_3$, $C_{1-6}$alkoxy, $C_{2-6}$alkenyloxy, $C_{2-6}$alkynyloxy, $C_{1-6}$alkylthio, $C_{2-6}$alkenylthio, $C_{2-6}$alkynylthio and —$O(CH_2)_pO$—;

Z is $Ar^4$;

$R^3$, and $R^4$, are independently as defined for $R^1$ and $R^2$;

$Ar^4$ is phenyl which is unsubstituted or subtituted with one or more groups independently selected from halogen, cyano, amino, nitro, $C_{1-6}$alkyl, $C_{2-6}$alkenyl, $C_{2-6}$alkynyl, $CF_3$, $C_{1-6}$alkoxy, $C_{2-6}$alkenyloxy, $C_{2-6}$alkynyloxy, $C_{1-6}$alkythio, $C_{2-6}$alkenylthio, $C_{2-6}$alkynylthio and —$O(CH_2)_pO$—;

k is 2;

m and n are 1; and p is 1; or 2.

2. A compound according to claim 1 wherein:

R is hydrogen, $C_{1-6}$ alkyl, $C_{2-6}$ alkenyl, $C_{2-6}$ alkynyl, $C_{1-6}$ alkoxy, $C_{2-6}$ alkenyloxy or $C_{2-6}$ alkynyloxy;

V is CH; and

W is O.

3. A compound according to claim 1, wherein:

Y is hydrogen, $NR^1R^2$, $C_{2-6}$ alkynyl, Ar, $O(CH_2)_nAr^1$ or $C_kH_{2k-4}Ar^2$;

$R^1$ and $R^2$ are independently selected from $C_{1-6}$ alkyl and $(CH_2)_mAr^3$;

Ar is pyridyl or pyrimidinyl and is unsubstituted or substituted with halogen or $C_{1-6}$ alkyl; unsubstituted naphthyl; or phenyl which is unsubstituted or substituted with $R^x$ and/or $R^y$ and/or $R^z$ wherein $R^x$ and $R^y$ are independently chosen from halogen, cyano, amino, nitro, $C_{1-6}$ alkyl, $C_{2-6}$ alkenyl, $C_{2-6}$ alkynyl, $CF_3$, $OCF_3$, $C_{1-6}$ alkoxy, $C_{2-6}$ alkenyloxy, $C_{2-6}$ alkynyloxy, $C_{1-6}$ alkylthio, $C_{2-6}$ alkenylthio, $C_{2-6}$ alkynylthio, hydroxy, hydroxy$C_{1-6}$alkyl, $NR^3R^4$, $OC(O)NR^3R^4$, $C_{1-6}$ alkoxyphenyl$C_{1-6}$alkoxy, cyano$C_{1-6}$alkyl, cyano$C_{2-6}$ralkenyl, cyano$C_{2-6}$alkynyl, pyridyl, phenyl, $C_{1-6}$ alkoxycarbonyl, $C_{1-6}$ alkoxycarbonyl$C_{1-6}$ alkyl, $C_{1-6}$ alkoxycarbonyl$C_{2-6}$ alkenyl, $C_{1-6}$ alkoxycarbonyl$C_{2-6}$alkynyl and —$O(CH_2)_pO$— and $R^z$ is halogen, $C_{1-6}$ alkyl or $C_{1-6}$ alkoxy and Ar is optionally fused to a benzene ring;

$Ar^1$, $Ar^2$ and $Ar^3$ are independently: pyridyl; or phenyl which is unsubstituted or substituted with halogen, cyano, amino, nitro, $C_{1-6}$ alkyl, $C_{2-6}$ alkenyl, $C_{2-6}$ alkynyl, $CF_3$, $C_{1-6}$ alkoxy, $C_{2-6}$ alkenyloxy, $C_{2-6}$ alkynyloxy, $C_{1-6}$ alkylthio, $C_{2-6}$ alkenylthio, $C_{2-6}$ alkynylthio or —$O(CH_2)_pO$—;

$R^3$ and $R^4$ are independently chosen from hydrogen and $C_{2-6}$alkyl;

k is 2;

m and n are 1; and p is 1 or 2.

4. A compound according to claim 1 which is:

5-benzyloxy-1-methyl-3-(4-methylthiazol-2-yl)-6-phenyl-1H-pyridin-2-one; or 5,6-diphenyl-1-methyl-3-(4-methylthiazol-2-yl)-1H-pyridin-2-one; or a salt thereof.

5. A pharmaceutical composition comprising a compound according to claim 1 or a salt thereof, and a pharmaceutically acceptable carrier.

6. A Process for producing a compound according to claim 1 in which V is CH which comprises:

reacting a compound of formula VII with with a compound of formula VIII:

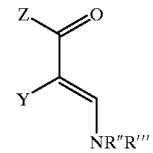

(VII)

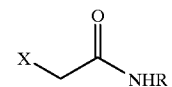

(VIII)

wherein R,X,Y and are as defined in claim 1 and R" and R'" are independently halogen or $C_{1-6}$ alkyl.

7. A method of treating or preventing anxiety or convulsions comprising administering to a subject in need of such treatment or prevention, a prophylactically or therapeutically effective amount of a compound according to claim 1, or a salt thereof.

8. A method of treating or preventing neuroses, migraine, and depressive or bipolar disorders comprising administering to a subject in need of such treatment or prevention, a prophylactically or therapeutically effective amount of a compound according to claim 1, or a salt thereof.

* * * * *